(12) United States Patent (10) Patent No.: US 8,418,929 B2
Tajima (45) Date of Patent: Apr. 16, 2013

(54) TEMPERATURE CONTROLLING APPARATUS AND TEMPERATURE CONTROLLING METHOD

(75) Inventor: Hideji Tajima, Matsudo (JP)

(73) Assignee: Universal Bio Research Co., Ltd., Matsudo-shi, Chiba (JP)

( * ) Notice: Subject to any disclaimer, the term of this patent is extended or adjusted under 35 U.S.C. 154(b) by 706 days.

(21) Appl. No.: 12/450,672

(22) PCT Filed: Apr. 7, 2008

(86) PCT No.: PCT/JP2008/056888
§ 371 (c)(1),
(2), (4) Date: Mar. 11, 2010

(87) PCT Pub. No.: WO2008/126827
PCT Pub. Date: Oct. 23, 2008

(65) Prior Publication Data
US 2010/0163111 A1 Jul. 1, 2010

(30) Foreign Application Priority Data
Apr. 6, 2007 (JP) ................................. 2007-101135

(51) Int. Cl.
*G05D 23/00* (2006.01)
*G01N 31/00* (2006.01)
*C12M 1/00* (2006.01)

(52) U.S. Cl.
USPC .............. 236/1 R; 422/50; 422/62; 422/68.1; 435/287.1

(58) Field of Classification Search .................. 236/1 C, 236/1 R; 422/50, 62, 68.1; 435/287.1
See application file for complete search history.

(56) References Cited

U.S. PATENT DOCUMENTS 4,683,202 A 7/1987 Mullis
5,720,923 A 2/1998 Haff et al.
(Continued)

FOREIGN PATENT DOCUMENTS

JP 05-308971 11/1993
JP 07-075544 3/1995
(Continued)

OTHER PUBLICATIONS

English Translation of International Search Report, Jul. 8, 2008, International Application No. PCT/JP2008/056888, Japanese Patent Office, 2 pages.

(Continued)

*Primary Examiner* — Marc Norman
(74) *Attorney, Agent, or Firm* — Haynes and Boone, LLP

(57) ABSTRACT

The present invention relates to a temperature controlling apparatus and the temperature controlling method which can arrest foaming and inflation of the air contained in a liquid, and can perform temperature controlling of a liquid of high reliance, and the present invention is constructed to have one or a plurality of sets of nozzles which can suck and discharge a liquid through a tip, and can retain the sucked liquid, a suction and discharge mechanism which can suck and discharge a gas via the each nozzle, a temperature regulator which can maintain one or two or more set predetermined temperatures for a predetermined time regarding one or two or more predetermined temperature controlling regions set in the each nozzle, a movement mechanism which allows relative movement between one or two or more containers which can accommodate a liquid and a nozzle, and a controlling part which instructs the movement mechanism, the suction and discharge mechanism or the temperature regulator to adjust a liquid to be sucked into the nozzle and a liquid amount thereof, a position of the sucked liquid in the nozzle, and temperature controlling of the liquid.

22 Claims, 21 Drawing Sheets

U.S. PATENT DOCUMENTS

| | | | |
|---|---|---|---|
| 5,958,349 A | 9/1999 | Petersen et al. | |
| 7,033,820 B2 * | 4/2006 | Ammann et al. | 435/287.1 |
| 2001/0018412 A1 | 8/2001 | Kambara | |
| 2007/0059206 A1 * | 3/2007 | Araki et al. | 422/65 |
| 2009/0298160 A1 | 12/2009 | Tajima et al. | |
| 2012/0171759 A1 * | 7/2012 | Williams et al. | 435/287.2 |

FOREIGN PATENT DOCUMENTS

| | | |
|---|---|---|
| JP | 08-121636 | 5/1996 |
| JP | 2000-342258 | 12/2000 |
| JP | 2001-145486 | 5/2001 |
| JP | 2005-249175 | 9/2005 |
| WO | WO 92/13967 | 8/1992 |
| WO | WO 97/46712 | 12/1997 |
| WO | WO 2006/038643 | 4/2006 |

OTHER PUBLICATIONS

Written Opinion of the International Searching Authority, Jul. 8, 2008, International Application No. PCT/JP2008/056888, Japanese Patent Office, 10 pages.

* cited by examiner (a)

(b)

TEMPERATURE CONTROLLING APPARATUS AND TEMPERATURE CONTROLLING METHOD

CROSS REFERENCE

This application is a United States national phase application of co-pending international patent application number PCT/JP2008/056888, filed Apr. 7, 2008, which claims priority to Japanese patent application number 2007-101135, filed Apr. 6, 2007, the disclosures of which are incorporated herein by reference.

TECHNICAL FIELD

The present invention relates to a temperature controlling apparatus and a temperature controlling method.

BACKGROUND ART

In recent years, as a DNA amplification method of amplifying a particular DNA fragment rapidly and easily, a polymerase chain reaction (PCR) method is used in every organism-related field. The PCR method is a method of designing two primers complementary with a template DNA, and replicating a region held by the primers in vitro. The method is to obtain a PCR product by amplifying a DNA exponentially by repeating a temperature cycle of incubating a reaction solution containing a template DNA, a primer, a nucleotide, and a heat-resistant DNA polymerase at various temperatures.

One time cycle including (1) denaturing a double-stranded DNA into single-stranded DNAs, (2) annealing primers to the single-stranded DNA, and (3) incubating it at respective temperature conditions (94° C., 50 to 60° C., and 74° C., respectively) under which a DNA chain complementary with the single-stranded chain is synthesized to extend a DNA, for a container containing a template DNA, a primer, a DNA polymerase, a nucleotide and a reaction buffer, thereby, and one molecule of a DNA fragment is rendered into two molecules. In the next cycle, since the DNA fragment synthesized in the previous cycle becomes a template, DNA fragments synthesized after n cycles become $2^n$ molecules.

Previously, in controlling of a temperature, a container made of a glass containing a template DNA, a primer, a DNA polymerase, a nucleotide and a reaction buffer is accommodated in an accommodating part of a block-like constant temperature device formed of a material of aluminum or the like, the block-like accommodation part made of a metal is heated or cooled, and one waits until a liquid temperature becomes an equal temperature distribution, thereby, next heating or cooling is performed (Patent Document 1).

For this reason, there is a problem that until a reaction solution in the container is heated or cooled, it takes a time to obtain equal liquid temperature distribution due to great volume of the container and, at the same time, complicated temperature change is generated due to a difference in heat capacity and specific heat between the accommodation part and the container, and it is necessary to perform complicated temperature controlling in order to amplify a DNA at a high precision.

Meanwhile, in the PCR method, controlling of a temperature is important, and quality and an amount of the finally obtained PCR product can be changed by changing a temperature cycle.

Particularly, in real time PCR, more precise quantitation is performed by detecting a process of producing an amplification product by PCR at real time, and analyzing this, and it is necessary to control a temperature at a higher precision and rapidly. For this reason, various apparatuses are proposed (Patent Document 2 to Patent Document 5). However, these apparatuses are large scale complicated apparatuses in which a complicated flow path is provided, and a large-scale centrifugation apparatus is used.

To the contrary, the present inventor disclosed a reaction container including a reaction container body provided with a reaction chamber accommodating a reaction solution, and a lid material capable of sealing an opening of the reaction chamber, wherein the lid material has a pressing part for pressing the reaction solution, thereby, it enabled to rapidly control a temperature at a scale of a simple apparatus without necessity of a centrifugal force (Patent Document 6).

In addition, the present inventor enabled to simultaneously shorten and automate a series of treatments with respect to PCR or the like without using a large-scale apparatus, by thinning or capillarizing a liquid having a high heat efficiency, and connecting reasonable centrifugation treatment and suction discharge treatment based on an especial shape of the container (Patent Document 7).

On the other hand, as an apparatus for implementing the PCR method, previously, an apparatus of applying a centrifugal force to introduce a liquid into a container in which a tube-like tip capillarized for enhancing following capability of thermal response is closed and control a temperature has been known. However, in the previous apparatus, since a bottom of the container is closed, it is difficult to completely remove the air, therefore, the apparatus has a problem that the air remaining on a bottom of the container may be dilated to fly the liquid introduced into the container to the inside and the outside of the container. In addition, the apparatus also has a problem that the gas contained in the liquid itself causes foaming, and this may impede uniform temperature controlling.

Then, the present inventor got an idea that, by utilizing the previously used dispensing apparatus having a nozzle with an open tip which enables suction and discharge of quantitation of an amount of a liquid, shortening of a treating time of, and automation of temperature controlling treatment for PCR, a series of treatments including light measurement, can be simultaneously performed at high reliance, without using a special container resulting from thinning or capillarizing a liquid, and without necessity of centrifugation treatment.

[Patent Document 1] Japanese Patent No. 2622327
[Patent Document 2] Japanese Patent Application National Publication (Laid-Open) No. 2000-511435
[Patent Document 3] Japanese Patent Application National Publication (Laid-Open) No. 2003-500674
[Patent Document 4] Japanese Patent Application National Publication (Laid-Open) No. 2003-502656
[Patent Document 5] U.S. Pat. No. 5,958,349
[Patent Document 6] Japanese Patent Application Laid-Open No. 2002-10777
[Patent Document 7] International Publication WO 2006/038643

DISCLOSURE OF THE INVENTION

Problems to be Solved by the Invention

Then, the present invention was done in order to solve the aforementioned problems, and a first object is to provide a temperature controlling apparatus and a temperature controlling method which can control a temperature of a liquid by a simple structure and simple control.

A second object is provide a temperature controlling apparatus and a temperature controlling method by which various treatments including temperature controlling can be effectively, consistently and automatically performed with respect to a liquid, a temperature of which is to be controlled.

A third object is to provide a temperature controlling apparatus and a temperature controlling method having a high reliance, which can assuredly prevent inhibition of uniform temperature controlling due to the air contained in a liquid introduced into a part where temperature controlling is performed, or the introduced air, or the generated foaming, flying to the inside and the outside of a container of a liquid due to inflation thereof, and accompanying cross contamination.

A fourth object is to provide a temperature controlling apparatus and a temperature controlling method which can control temperatures of a plurality of different subjects parallel.

Means to Solve the Invention

A first aspect of the invention is a temperature controlling apparatus including one or a plurality of sets of nozzles which can suck and discharge a liquid through a tip, and can retain the sucked liquid, a suction and discharge mechanism which can suck and discharge a gas via the each nozzle, a temperature regulator which can maintain one or two or more set predetermined temperatures for a predetermined time regarding one or two or more predetermined temperature controlling regions provided in the each nozzle, a movement mechanism which allows relative movement between one or two or more containers which can accommodate a liquid and the nozzle, and a controlling part which instructs the movement mechanism, the suction and discharge mechanism or the temperature regulator to adjust a liquid to be sucked into the nozzle and a liquid amount thereof, a position of the sucked liquid in the nozzle, and temperature controlling of the liquid.

Here, the "nozzle" is a flow path for sucking or discharging a fluid through a tip, and examples include a flow path in which a whole nozzle is integratedly formed, and a flow path in which the flow-path formed in another body is bound or connected for use, so as to attach a disposable tip to an attachment nozzle. In addition, as the disposable tip itself, there is a disposable tip in which the disposable tip formed in another body is bound or connected for use. The nozzle or the disposable tip can be produced with organic materials such as resins, for example polypropylene polystyrene, polyester, polyethylene, acryl, or inorganic materials such as glasses, ceramics, metals such as stainless steel, metal compounds, semiconductors or the like. As a size, for example, a liquid of about a few µ liter to a few hundreds µ liter, preferably about a few µ liter to 20µ liter can be accommodated. When two or more nozzles are provided, they are arranged in one row manner or a matrix manner at a constant interval so as to correspond to arrangement of the container or the like.

The "temperature controlling region" is a region which is a part of the nozzle, in which the region itself or a liquid situated at the region can be maintained at one or two or more set predetermined temperatures. The temperature controlling region is determined by a temperature raising or lowering body of a temperature regulator, a constant temperature source, a heat-producing part facing a nozzle of a liquid source, a shape, a size, a heat amount, and its installation position (including a distance between a nozzle and a part faced by the nozzle) of a heat-producing part, a cooling part or an ejection pore part, or the like. The temperature controlling region is, for example, a part of a nozzle corresponding to a heat-producing part, a cooling part or an ejection pore facing a nozzle of the temperature raising or lowering body, the constant temperature source, or the fluid source, or a part of a nozzle in a region of conduction of heat corresponding to a temperature set with respect to the heat-producing part or the like, or in a region of radiation of a corresponding heat ray, or in a region of release of a fluid corresponding to a set temperature. In order that a temperature is uniformly maintained, it is preferable that the temperature controlling region is within a range which can rapidly and truthfully temperature control with the temperature regulator. In addition, in the temperature controlling region, among the nozzle, a part having such a shape that a shaft center is straight, and the same predetermined internal diameter is possessed is preferable for adjusting a position of a liquid or a controlling temperature uniformly. It is preferable that two or more temperature controlling regions are provided so that they are a part at a predetermined interval.

It is preferable that the temperature controlling region is determined so that the region does not contain a front end of the nozzle and a rear end of the nozzle, or dose not approach them. That is, it is preferable that from a lower end to a tip end of the temperature controlling region, and from an upper end to a rear end of the temperature controlling region are determined around a central part of the nozzle so that they are isolated at an appropriately interval. It is preferable that the temperature controlling region, in the case of the disposal tip, is set around a central part of a small diameter tube. Thereby, discharge of a liquid from the nozzle can be prevented, and disturbance of a temperature distribution due to influence from an external part at a periphery of the nozzle can be eliminated. In addition, it is preferable that the temperature controlling region is formed of a material having high heat conductivity such as a metal such copper or stainless steel, and tubes having a length to the extent of covering the temperature controlling region, and having an external diameter approximately equal to an internal diameter of the nozzle are concentrically provided. It is preferable that a number of penetrating pores are provided in the tube.

The "predetermined temperature" is a temperature which is a goal to which a subject gets, for example, in the case of amplifying a nucleic acid such as a DNA, and an oligonucleotide or the like contained in the liquid by the PCR method, a predetermined temperature to be set is each temperature necessary in a temperature cycle performed in the PCR method, that is, for each of denaturation, annealing and elongation of a DNA, a temperature of about 94° C., and between 50 to 60° C., for example, about 50° C. and about 72° C. Further, the predetermined temperature includes, for example, a temperature for promoting transfer for shortening a transfer time to render a one cycle time within a predetermined cycle time by performing cooling at a further lower temperature for promoting transfer than the predetermined temperature with a temperature regulator, for transfer from a predetermined temperature of a high temperature to a predetermined temperature of a low temperature, or by performing heating at a further higher temperature for promoting transfer than the predetermined temperature, upon transfer from a predetermined temperature of a low temperature to a predetermined temperature of a high temperature. The "predetermined time" is a necessary time for maintaining of each temperature, and depends on reagents and liquid amounts used in the PCR method, and a shape, a material, a size and a thickness of the nozzle, and one cycle is a total of, for example, a few seconds to a few tens seconds, and a processing time as a whole of the PCR method is, for example, a few minutes to about a few tens minutes. The transfer time is also included in the predetermined time.

"Temperature controlling of the liquid" is instruction of execution of determined times according to a determined order to maintain a liquid to be temperature-controlled situated at the one or two or more temperature controlling regions at one or two or more set temperatures for set times. The "instruction" is conducted by sending an electronic signal corresponding to the instruction to the transfer mechanism or the like.

"Adjustment of a position" is performed so that a central part of a liquid entire length of a sucked liquid in the nozzle along an axial direction of the nozzle is consistent of a central part of a region entire length of the temperature controlling region along an axial direction of the nozzle, based on, for example, an amount of a liquid to be sucked, and an internal diameter of the nozzle in the temperature controlling region. Thereupon, depending on an amount of a liquid, an entire length of a liquid may exceed an entire length of the temperature controlling region in some cases, but since a liquid part to be temperature-controlled is a liquid of a part corresponding to the temperature controlling region, it is necessary to perform treatment of removing a run-over liquid part in some cases. Besides, adjustment of a position includes transfer of a liquid between two or more temperature controlling regions depending on an order or a time. When two or more temperature controlling regions are provided in one nozzle, and different predetermined temperature are set, respectively, a liquid to be temperature-controlled is subjected to position adjustment so that the liquid is transferred between the temperature controlling regions in the nozzle. In addition, when two or more predetermined temperatures are set for one temperature controlling region, a temperature regulator is controlled so that different set predetermined temperatures are sequentially produced, and maintained, while the liquid is position-adjusted so as to stay in the same temperature controlling region.

A second aspect of the invention is the temperature controlling apparatus, wherein the controlling part instructs the movement mechanism or the suction and discharge mechanism to choke and pressurize the nozzle below the temperature controlling region of the nozzle upon temperature controlling.

Herein, since the nozzle is choked below the temperature controlling region, pressurizing may be performed while ejection of a liquid in the temperature controlling region is arrested upon temperature controlling. For choking the nozzle, for example, the nozzle is moved so as to push a tip of the nozzle against a bottom of a flat container, or a stage, or the nozzle is choked using a choking member described later. By choking of the nozzle, a liquid is introduced below the temperature controlling region highly probably flying the liquid without introducing a small amount of the air and, at the same time, foaming a minor amount of the dissolved air which may occur upon repetition of heating and cooling upon temperature control by pressuring, and inflation of a minor amount of the air unintentionally introduced below the temperature controlling region can be arrested, thereby, a position in the nozzle can be assuredly adjusted, and uniform temperature control can be performed. In addition, cross contamination due to flying in a liquid nozzle by inflation of the produced bubbles and inflation of the air introduced below the temperature controlling region can be prevented. A magnitude of pressurizing is pressuring to such the extent that inflation of a minor amount of dissolved or introduced bubbles can be arrested, and may depend on a temperature and a liquid amount and, for example, is around 1.1 atom to around 2 atom.

A third aspect of the invention is the temperature controlling apparatus, wherein the nozzle includes a mounting nozzle and a disposable tip including a mounting opening detachably mounted on to a mounting nozzle and a mouth part which can suck and discharge a liquid at a tip, and the temperature controlling region is provided in the disposable tip.

Mounting is performed by inserting a tip of the mounting nozzle into, and fitting with an opening for mounting of the disposable tip. For this reason, a tip rack in which the mounting nozzle mountably accommodates the disposable tip by fitting is provided, and the mounting nozzle is provided relatively movably between the tip rack by the moving mechanism. For detachment of the disposable tip, for example, a detachment member provided with pores, cavities or gaps having such an internal diameter or width that the mounting nozzle can pass, but amounted disposable tip cannot pass is provided above the mounting nozzle, so that the member can be moved up and down along an axial direction while the mounting nozzle and the disposable tip is held in the pores or the gaps. By moving the detachment member downwardly, the disposable tip is detached from the mounting nozzle so as to scrape off the tip.

A fourth aspect of the invention is the temperature controlling apparatus, wherein the nozzle includes a large-diameter tube, a small-diameter tube formed to be thinner than the large-diameter tube, and the transition part formed between the large-diameter tube and the small-diameter tube, and the temperature controlling region is set in the small-diameter tube.

Herein, since the temperature controlling region is set in the most thinly formed small-diameter tube, it has high following capability to temperature control from the outside.

A fifth aspect of the invention is the temperature controlling apparatus, the small-diameter tube is formed so that an axis is straight, and an internal diameter thereof is a constant size along an axial direction, and a size of an internal diameter thereof is 3 mm or less and 0.1 mm or more.

A size of this internal diameter is thinness to such an extent that uniform temperature controlling becomes possible. When the internal diameter is great, since a temperature difference is generated in a liquid in the nozzle by temperature controlling, heat convection due to downward movement of a liquid having a low temperature and upward movement of a liquid having a high temperature is generated, there is a possibility of unevenness of a temperature distribution, and difficulty in position adjustment due to foaming or mixing of the gas or bubbles, or cross contamination due to flying of a liquid in the nozzle by thermal inflation of the gas or bubbles. Further, in the temperature controlling region, it is preferable to make adjustment of a position of a liquid in the nozzle easy by a shaft center being straight, and an internal diameter being constant along an axial direction. The internal diameter is further preferably 0.5 mm to 1 mm. It is preferable that the wall thickness of the small-diameter tube is sufficiently small as compared with the internal diameter since following capability to temperature controlling is increased, and a temperature distribution in the nozzle becomes uniform. The wall thickness is preferably a size smaller than the internal diameter, for example, around 0.2 mm.

A sixth aspect of the invention is the temperature controlling apparatus, wherein the temperature regulator includes one or two or more temperature raising and lowering bodies which are provided so as to contact with or come close to a side wall of the temperature controlling region of the nozzle, and can raise and lower a temperature.

Herein, as the "temperature raising and lowering body", for example, there are a body which enables heating and cooling at various temperatures by a direction of flow of a current using a Peltier element, a heater which can make a heating temperature variable by an intensity of a current.

A seventh aspect of the invention is the temperature controlling apparatus, wherein the temperature regulator includes one or two or more temperature controlling sources which are provided so as to relatively come close to or to be departed from a side wall of the temperature controlling region of the nozzle, and are set at a predetermined temperature.

Herein, the "temperature constant source" is, for example, an electric heater equipped with a Peltier element or a thermostat set at a predetermined temperature.

An eighth aspect of the invention is the temperature controlling apparatus, wherein the temperature regulator includes one or two or more fluid sources which flow a fluid at a predetermined temperature so as to contact with or come close to the temperature controlling region of the nozzle.

Herein, the "fluid source" is an apparatus for flowing a gas or a liquid so as to contact with the nozzle, for example, an ejection mechanism such as a blower, a fan, a pump or the like, and a fluid may be flowed through a flow path provided separately from the nozzle, so as to reach a predetermined external region surrounding the temperature controlling region, and the fluid is discharged through a flow path from the external region.

A ninth aspect of the invention is the temperature controlling apparatus, wherein the temperature regulator includes a temperature regulating chamber in which the nozzle penetrates the interior thereof, and which surrounds an external surface of the nozzle corresponding to the temperature controlling region of the nozzle, an inlet which is provided in the temperature regulating chamber, and in which a fluid flowed from the fluid source can be flowed into the interior, and an outlet which is provided in the temperature regulating chamber, and flows out the flowed in fluid from the interior through the inlet.

In addition, the "temperature adjustment chamber" is preferably formed to be dividable into two parts with a plain containing an axial direction of the nozzle, for example, so that it can be assembled so as to hold the nozzle from both sides.

A tenth aspect of the invention is the temperature controlling apparatus, wherein the nozzle is provided so that it can be moved relative to the temperature raising and lowering body, the constant temperature source or the fluid source by the movement mechanism.

The case where both can be moved to each other, such as the case where the nozzle is moved to a temperature raising and lowering body or the like of a fixed temperature regulator and, the temperature raising and lowering body or the like is moved to (approaches or gets away from) the temperature controlling region of the nozzle, is also included.

An eleventh aspect of the invention is the temperature controlling apparatus including a light measuring equipment for measuring light emission in the temperature controlling region of the nozzle.

Therefore, as a premise of realizing the present invention, it is necessary that at least a part of a material forming the nozzle has translucency. In addition, light to be measured includes fluorescence, phosphorescence, chemiluminescence and the like. A light measuring equipment has at least a light receiving part and, in the case of fluorescence and phosphorescence, has an irradiation part for irradiating light for excitation. A light receiving direction or an irradiation direction of each edge face of the light receiving part or the irradiation part is along an axial direction of the nozzle, or orthogonal with an axial direction of the nozzle. Alternatively, the light receiving part or the irradiation part may be provided in any of the interior and the outside of the nozzle.

The light measuring equipment is provided for obtaining optical information in the nozzle, for example, for measuring an amount and a concentration of a genetic substance such as a DNA and the like labeled with fluorescence, by real time PCR. Herein, the "real time PCR" is a method of performing PCR while an amplification amount of a DNA is measured at real time. Real time PCR has an advantage that electrophoresis is not necessary, amplification can be observed during a temperature cycle, and quantitative result is obtained. Usually, as a method of performing real time PCR using a fluorescent reagent, there are a cycling probe method, an intercalator method, a TaqMan probe method and a Molecular Beacon method.

Further, in the present invention, it is also possible to perform light measurement after completion of temperature controlling, not during a temperature cycle.

In addition, the light measuring equipment may have, for example, two or more irradiation ends provided at each irradiation position, a plurality kinds of light sources for generating lights having a plurality kinds of wavelength, respectively, a light source selection part for selecting one kind of light among lights from the light sources by temporal switching, and introducing lights to the each irradiation end at once, two or more light receiving ends provided at two or more respective light receiving positions, a light receiving position-selection part for selecting lights from the respective light receiving ends by temporal switching, an optical filter selection part for selecting a plurality of kinds of optical filters through which light from the selected light receiving position should pass, by temporal switching, and a photoelectric element for sequentially inputting light from the selected light receiving position and having passed through the selected optical filter. Thereby, even when two or more labeling substances are used for the nozzle, since processing may be performed using a few photoelectric elements by temporally switching a kind of a labeling substance to be a subject of a labeling substance, an apparatus scale as a whole can be reduced or simplified.

Herein, a plurality of kinds of optical filters are provided, for example, in the case where a labeling substance of outputting a plurality of kinds of light wavelengths for labeling a DNA fragment, an amount or a concentration of which is to be measured, by real time PCR in the nozzle. Thereby, the presence or an amount of the corresponding labeling substance can be measured by transmitting light having each wavelength through an optical filter.

The "photoelectric element" includes an electronic element utilizing the photoelectric effect, such as phototube, photomultiplier, a photoconducting cell, a phototransistor, a photodiode and the like.

In addition, the irradiation end is formed, for example, of a rod lens. In addition, the rod lens can perform light irradiation having a good deficiency by providing it so as to contact with or get away from the nozzle, allowing regulation of a focal point distance.

In addition, the light measuring equipment has one or two or more irradiation ends for irradiating light to the nozzle, and one or two or more light receiving ends for receiving light from the nozzle, the irradiation end and the light receiving end are provided outside the nozzle or a nozzle head, and it may be provided so as to contact with or come close to the nozzle by a moving mechanism, or contactably therewith and releasably therefrom.

Further, the light measuring equipment has one or two or more irradiation ends for irradiating light to the nozzle, and one or two or more light receiving ends for receiving light from the nozzle, the irradiation end of the light measuring equipment is provided in the nozzle or a nozzle head, and may be provided so as to contact with or come close to the temperature controlling region of the nozzle, or contactably and therewith and releasably therefrom. When the irradiation end or the light receiving end is provided in the nozzle, for example, it may be provided so that an axial direction of the nozzle and a normal line direction of the irradiation edge face or the light receiving edge face are consistent. In addition, in the case of a nozzle which is used by mounting a disposable tip in a mounting nozzle, the irradiation edge face or the light receiving edge face is provided on a lower edge face of the mounting nozzle. Thereupon, the irradiation edge face or the light receiving edge face may be formed annularly.

A twelfth aspect of the invention is the temperature controlling apparatus, wherein a nozzle choking member which can choke the nozzle to prevent flow-out of a fluid from the nozzle is provided below a temperature controlling region of the nozzle or the outside of the nozzle, and further includes an on-off mechanism which opens and closes the nozzle below the temperature controlling region using the choking member.

Herein, the "nozzle choking member" is a fixed cap having an on-off valve provided below the temperature controlling region of the nozzle, or a pin which is provided outside the nozzle so as to be fittable with a tip of the nozzle, and fixedly provided protruding upwardly to be inserted into a mouth part at a tip of the nozzle to choke it, or a fixed cap having no pin, or a movable cap which is positioned out side the nozzle so as to be fittable with a tip part pf the nozzle which is fitted so as to cover a tip of the nozzle by insertion of a tip of the nozzle, having the pin or not having the pin.

In addition, the on-off mechanism, when the choking member is an on-off valve provided in the nozzle, for example, is magnetic force means for moving a valve made of a magnetic material to open and close the nozzle by a remote action such as a magnetic force and the like and, when the choking member is the fixed cap or the movable cap, is a moving mechanism which relatively moves between the nozzle and the fixed cap or the movable cap. In addition, by forming a choking member fittably provided at a tip of the nozzle, or a part thereof, of a heat-shrinking material like the fixed cap or the movable cap, high adherability with the nozzle can be attained, and secure choking is possible by heating the choking member to shrink it. In addition, since heating can be performed by the temperature regulator, it is not necessary to add a new on-off mechanism. Therefore, choking of the nozzle can be assuredly performed without extending an apparatus scale. Moreover, since a cylinder part of the choking member fitting with a tip of the nozzle can be formed large by using the heat-shrinking material, insertion of a tip of the nozzle is smooth and easy, and damage of a tip of the nozzle and the choking member can be prevented. Herein, examples of the "heat-shrinking material" include resins such as fluorine, nylon, urethane, vinyl chloride (e.g. flame-retardant hard polyvinyl chloride-based, soft polyvinyl chloride-based), polyolefin, polybutene, polyethylene, silicone.

A thirteenth aspect of the invention is the temperature controlling apparatus, wherein the nozzle is provided movably relative to a container capable of accommodating a liquid to be temperature-controlled, and a container capable of accommodating a sealing liquid for sealing the liquid in the nozzle by holding it from upper and lower directions in the nozzle by the movement mechanism.

Herein, the "sealing liquid" is a liquid which can hold a liquid to be temperature-controlled from up and down without mixing in with, or mixing of it and, generally, an upper sealing liquid and a lower sealing liquid are usually different, and the upper sealing liquid and the lower liquid may be the same. In addition, by sucking a liquid to be temperature-controlled at such an amount that exceeds the temperature controlling region, it can be used as the upper sealing liquid or the lower sealing liquid, for a part among the liquid to be temperature-controlled. As the sealing liquid, for example, an inorganic-derived oily liquid used for forming an oil film for preventing evaporation used in PCR, for example, a mineral oil is used. Thereby, since influence of temperature controlling of the liquid to be temperature-controlled does not influence on upper and lower air accommodating parts by the sealing liquid, inflation and shrinkage of the air at that part can be prevented. In addition, an air layer unintentionally introduced accompanied with suction may be presented between, particularly, the lower sealing liquid and the liquid to be temperature-controlled, but an amount is very small, and since inflation can be arrested by the pressuring, flying of a liquid can be prevented (even when an air layer or the air on an upper side of the temperature controlling region is inflated, since it only pressurizes the liquid to be temperature-controlled, it does not lead to flying of a liquid with difficulty).

A fourteenth aspect of the invention is the temperature controlling apparatus, wherein the apparatus includes a movable cap which is fittable with a tip of the nozzle, and can be conveyed, or a fixed cap which is fittable with a tip of the nozzle, and cannot be conveyed, as the choking member, the nozzle is provided movably relative to the movable car or the fixed cap, or the on-off mechanism includes the movement mechanism.

The "movable cap" is a cap movable with a mounted nozzle and, for example, has a cylinder with bottom which is fittable with a tip part of the nozzle, or a pin or a rod which is fittable by protruding into a center of the cylinder with bottom, and inserting into a tip of the nozzle. The "fixed cap" is a cap which cannot be moved with amounted nozzle, and there are, for example, a pin or a rod fixed on the stage which is fittable with the tip of the nozzle, and is protruded upwardly, an annular groove with which the tip of the nozzle is fitted, and the cylinder. Thereby, mounting of the disposable tip, and choking of the nozzle can be automatically performed by moving the nozzle head.

A fifteenth aspect of the invention is the temperature controlling apparatus, wherein the light measuring equipment includes at least a light receiving end, and the nozzle is provided movable relative to the light receiving end by the movement mechanism.

A sixteenth aspect of the invention is a temperature controlling method including: a suction step of moving one or a plurality of sets of nozzles relative to one or two or more containers accommodating a liquid, and sucking a designated liquid amount of a designated liquid into one or a plurality of sets of nozzles, a liquid position adjusting step of positioning the liquid in any of one or two or more temperature controlling regions set at one or two or more predetermined temperatures, respectively, set in the each nozzle, based on the liquid amount, and a temperature controlling step of performing temperature controlling of the liquid situated at the temperature controlling region.

A seventeenth aspect of the invention is the temperature controlling method, wherein in the temperature controlling step, the nozzle is choked, and a liquid is pressurized below the temperature controlling region of the nozzle.

An eighteenth aspect of the invention is the temperature controlling method, wherein the nozzle includes a mounting nozzle, and a disposable tip which is detachably mounted in the mounting nozzle, and the method includes a mounting step of mounting the disposable tip in the mounting nozzle before the suction step.

A nineteenth aspect of the invention is the temperature controlling method, wherein the temperature controlling step includes a step of raising or lowering a temperature of one or two or more temperature raising and lowering bodies provided so as to contact with or come close to a side wall one or two or more temperature controlling regions of the nozzle.

A twentieth aspect of the invention is the temperature controlling method, wherein the temperature controlling step includes a step of relatively making one or two or more constant temperature sources set at one or two or more predetermined temperatures come close to or being departed from a side wall of one or two or more temperature controlling regions of the nozzle.

A twenty-first aspect of the invention is the temperature controlling method, wherein the temperature controlling step flows a fluid of one or two or more predetermined temperatures using a fluid source so as to contact with or come close to the one or two or more temperature controlling regions of the nozzle.

A twenty-second aspect of the invention is the temperature controlling method, wherein the temperature controlling step includes a step of moving the temperature raising and lowering body, the constant temperature source or the fluid source relative to the one or two or more temperature controlling regions of the nozzle.

In addition, it is preferable that there is a choking step of choking the nozzle below the temperature controlling region using the choking member, before the temperature controlling step or after the liquid position adjusting step. The choking step is performed using the on-off mechanism.

A twenty-third aspect of the invention is the temperature controlling method further including a light measuring step of measuring light in the temperature controlling region of the nozzle.

The light measuring step is, for example, such that light is received in a cavity of the nozzle.

A twenty-fourth aspect of the invention is the temperature controlling method, wherein the suction step sucks the liquid to be temperature-controlled at a liquid amount to a degree of overflowing the temperature controlling region in the nozzle, and the position adjusting step adjusts a position so that the liquid overflows the temperature controlling region at upper and lower positions.

A position is adjusted, for example, so that overflow liquid amounts become equal between upper and lower locations, or the liquid amount is larger on a lower side. When a temperature-controlled liquid is discharged and utilized, the liquid is discharged so that only a liquid in the temperature controlling region is utilized, and a liquid outside the temperature controlling region is discarded, and is not utilized.

A twenty-fifth aspect of the invention is the temperature controlling method, wherein the suction step includes a step of sucking an upper side sealing liquid, a step of sucking the liquid to be temperature-controlled, and a step of sucking a lower side sealing liquid.

In addition, the upper sealing liquid and the lower sealing liquid may be the same liquid.

A twenty-sixth aspect of the invention is the temperature controlling method further including a step of discharging a liquid accommodated in the nozzle into one or two or more containers.

A discharged liquid is further used in analysis of an objective substance contained in the liquid, further processing regarding the objective substance, and treatment utilizing the objective substance. In this case, where the nozzle is subjected to choking treatment upon the temperature controlling step, it is necessary that treatment of choking the nozzle is stopped, and treatment of opening the nozzle is performed.

A twenty-seventh aspect of the invention is the temperature controlling method, wherein in the light measuring step, any liquid of a plurality of kinds of liquids to be sucked is colored. The colored liquid includes a liquid to be temperature-controlled, or the sealing liquid, and includes the case where a sucked entire liquid is distinguishably colored.

A twenty-eighth aspect of the invention is a disposable tip including a large-diameter tube including a mounting opening which can be directly or indirectly mounted on to a mounting nozzle where a gas is sucked and discharged, a small-diameter tube which is formed to be thinner than the large-diameter tube, and includes a mouth part in which a fluid is sucked and discharged, and a transition part provided between the large-diameter tube and the small-diameter tube, in the small-diameter tube, a choking member which openably and closably chokes the small-diameter tube is provided below one or two or more temperature controlling regions maintained at one or two or more set predetermined temperatures.

A twenty-ninth aspect of the invention is the disposable tip, wherein the choking member includes an extremely small tube which is fitted and connected to a tip of the small-diameter tube, and is formed to be thinner than the small-diameter tube, a sealing part which is provided below the temperature controlling region of the small-diameter tube, and is provided so as to narrow the interior of the small-diameter tube, and an on-off valve including a valve body including a magnetic body which is movably sealed in the small-diameter tube between the sealing part and the extremely-small tube, the sealing part makes a liquid pass, but arrests passage of the valve body, and the valve body can choke an upper end opening of the extremely-small tube.

The valve is, for example, spherical, mushroom-like, cone-like, cylindrical, block-like or the like, the valve is on-off-driven with a magnetic force device and, for choking, the valve is moved downwardly by the magnetic force device to adhere to an upper end of the extremely thin tube to choke it and, for opening, opening is performed by moving the valve upwardly. The magnetic force device corresponds to the on-off mechanism. The disposable tip of the twenty-eight aspect or the twenty-ninth aspect of the invention in which a plurality of particle-like carriers or an aggregate of a plurality of sets of particle-like carriers is encapsulated into the temperature controlling region, corresponds to the particle-like carrier-encapsulated tip.

A thirtieth aspect of the invention is a tool capable of temperature controlling, wherein in the temperature controlling region of the nozzle, a plurality of kinds of chemical substances are fixed, a plurality of fixable particle-like carriers, or an aggregate of a plurality of sets of particle-like carriers is sealed in the nozzle so as to contact with a sucked liquid and, at the same time, particle-like carriers or an aggregate of particle-like carriers to which the chemical substance is fixed or can be fixed, and the chemical substance are associated so as to be measured from the outside.

Herein, the "plurality of kinds of chemical substances", that is, various substances are chemical substances of a plurality of kinds of biological substances or the like, for example, chemical substances including biological polymers or low-molecular substances such as genetic substances such as nucleic acids, proteins, sugars, sugar chains, peptides and the like, and the biological substances detect binding of, capture, and separate biological substances as a receptor having binding property with the biological substances as a ligand, and a used in extraction or the like. The receptor corresponds to biological substances such as genetic substances such as nucleic acids, proteins, sugar chains, peptides and the like, each having binding property with the genetic substances such as nucleic acid, the proteins, the sugar chains, the peptides and the like. In addition, as the biological substances, or in place of biological substances, living bodies themselves such as cells, viruses, plasmids can be used.

The "fixation" refers to binding of at least one kind of the chemical substances to the particle-like carrier directly or indirectly via another kind of substance. As the binding, there are, for example, bindings due to physical adsorption, hydrogen bond, and electric interaction in addition to bindings due to covalent bond, and chemical adsorption. Alternatively, the chemical substance is fixed to a binding substance possessed by the particle-like carrier by a specific reaction between various substances, or other method. Alternatively, by forming the particle-like carrier of a porous substance, an irregular substance, or a fibrous substance, the ability of reacting with, or the ability of binding with various substances maybe enhanced. For fixation, a functional group is manifested or generated on the particle-like carrier. For doing so, by hydrolyzing a peptide bond possessed by silk, various nylons, wholly aromatic polyamides such as PPTA (polyparaphenyleneterephthalamide), heterocycle-containing aromatic polymers or the like, including a "polyamide-based polymer", a functional group used in fixation of biological substances is manifested, or generated. As a functional group capable of binding with biological substances, there are a carboxyl group-COOH, an amino group-$NH_2$ or the like, or a derivatized group thereof, for example. Herein, a porous diameter suitable for fixing biological substances is, for example, a few micrometers or smaller.

The "particle-like carrier" is a particle-like solid having such a size that it can be introduced into the nozzle, and retained therein. A size of the particle-like carrier is, for example, such that a diameter has a size of 0.1 mm to a few mm. In the temperature controlling region of the nozzle, retaining the particle-like carrier, a volume thereof is such that a space part except for the retained particle-like carrier is a volume of, for example, a few μ liter to a few hundreds microliter.

A material of the "particle-like carrier" is a substance insoluble in a liquid sample, and there are metals, semiconductors, half metals, metal compound such as metal oxides, inorganic substances such as ceramics, glasses, and silica, and organic substances such as resins such as rubber, latex, polystyrene, polypropylene, polyester, acryl and the like, cellulose, polymer substances such as fibrous substances such as nylon and the like, and natural fibrous substances and the like.

The "aggregate of particle-like carriers" is an aggregate of particle-like carriers to which at least two particle-like carriers belong, and the particle-like carrier belonging to the aggregate is specified by the predetermined number, by a predetermined distance between belonging particle-like carriers, by a predetermined range in which the particle-like carrier is situated, or by a predetermined boundary, film or case surrounding the belonging particle-like carrier. Thereby, the aggregate of particle-like carriers can be also handled as a whole as if it is one particle-like carrier. In addition, functions may be dispersed into every particle to make handling easy, or other various functions may be added, such as a particle-like carrier having the function of immobilizing various substances, a particle-like carrier having the function of labeling, and other particle-like carrier (for showing a boundary between aggregates, or sealing light so that lights generated by labeling are not mixed). In addition, as far as the aggregate of the particle-like carriers can be clearly distinguished, since the number of particle-like carriers belonging thereto can be freely set, there are extending property, general-use, and diversity.

Being "measurable from the outside", at least a part of the nozzle becomes to have translucency. For "encapsulation", a filter provided so as to partition the nozzle, or a step or a protrusion part provided by processing an inner wall of the nozzle is used.

"Retained in the generally stationary state" referred to the state where each particle-like carrier is not freely moved in the temperature controlling region in the nozzle, but each particle-like carrier is measurably generally stationary relative to other particle-like carrier, or the nozzle, or an introduced liquid. However, it is not necessary that each particle-like carrier is completely immobilized.

In addition, not only the case where by introducing respective particle-like carriers into the nozzle in a predetermined sequence, and retaining them therein, carriers become to be first distinguishable from its positional information (including order information), but also the case where by binding a distinguishable label element to the particle-like carrier itself, or by distinguishably processing or forming the particle-like carrier itself, they are distinguished, are included.

A thirty-first aspect of the invention is the temperature controlling method, wherein in the temperature controlling region of the nozzle, a plurality of kinds of chemical substances are fixed, a plurality of fixable particle-like carriers, or an aggregate of a plurality of sets of particle-like carriers is sealed in the nozzle so as to contact with a sucked liquid and, at the same time, particle-like carriers or an aggregate of particle-like carriers to which the chemical substance is fixed or can be fixed, and the chemical substance are associated so as to be measured from the outside.

Effects of the Invention

According to the first or sixteenth aspect of the invention, after a liquid to be temperature-controlled is sucked into the nozzle, and is situated in the temperature controlling region, temperature controlling is performed only in the temperature controlling region. Since a tip of the nozzle is opened, below the temperature controlling region, a liquid can be introduced up to a tip without introducing the air. Therefore, by temperature-controlling in the temperature controlling region, outside the temperature controlling region, particularly below the region, the situation where the introduced air is inflated, and a liquid to be temperature-controlled is flied to inside and the outside of the nozzle can be prevented. For this reason, cross contamination can be assuredly prevented, and high reliance treatment can be performed.

Since temperature is controlled via a temperature regulator provided in the outside only in one or two or more temperature controlling regions set into a nozzle which can suck and discharge a liquid, suction of a liquid, temperature controlling, light emission measurement and the like can be consistently and automatically processed using the same apparatus.

Treatment is not performed such that a liquid is transferred from a container accommodating a liquid to be temperature-controlled to a container in which temperature controlling is performed, and a temperature is controlled, and a liquid whose temperature controlling has been completed is moved to another container, but a temperature of a sucked liquid is controlled in the nozzle itself used for transfer from a container to a container, thereby, treatment can be performed rapidly and effectively.

According to the second or seventeenth aspect of the invention, by choking the nozzle below the temperature controlling region of the nozzle, and pressuring a liquid without discharging it upon temperature controlling, foaming of a gas dissolved in a liquid itself introduced so that there is little gas below the temperature controlling region can be arrested. Therefore, a position of a liquid is not slipped by foaming, and transmission of heat is not impeded, positional adjustment can be assuredly and easily performed and, at the same time, uniform temperature controlling can be performed. In addition, since cross contamination due to flying of a liquid inside and outside the nozzle resulting from inflation of the generated bubbles can be assuredly prevented, high reliance temperature controlling of a liquid can be performed.

According to the third or eighteenth aspect of the invention, by mounting the disposable tip in the mounting nozzle, and providing the temperature controlling region in the disposable tip, cross contamination can be prevented, and high reliance treatment can be performed without including a washing step.

According to the fourth aspect of the invention, the nozzle is formed to be constructed of a large-diameter tube, a small-diameter tube and a transition part, and the temperature controlling region is set in the small-diameter tube. Therefore, following capability of temperature controlling with a temperature regulator from the outside is high, and temperature controlling can be assuredly performed.

According to the fifth aspect of the invention, the small-diameter tube is formed so that its axis is straight, and its internal diameter is constant over its full length along an axial direction. Therefore, for the set temperature controlling region, uniform temperature controlling having high following capacity can be performed with a temperature regulator at the outside. In addition, since a size of its internal diameter is 3 mm or smaller and 0.5 mm or larger, positional controlling is easy in spite of in the small-diameter tube.

According to the sixth or nineteenth aspect of the invention, by raising or lowering a temperature of the temperature raising and lowering body provided so as to contact with or come close to a side wall of the nozzle, the temperature controlling region can be assuredly maintained at a set temperature without necessity of transfer for temperature controlling of the nozzle and the temperature raising and lowering body.

According to the seventh or twentieth aspect of the invention, since a constant temperature source is provided to be relatively come close to and get away from relative to a side wall of the temperature controlling region, the constant temperature source is retained at a pre-set temperature, and transfer imparts influence of a temperature of the constant temperature source on the temperature controlling region, therefore, temperature controlling can be rapidly and assuredly performed only by a transfer time in place of a time until a temperature is transferred to a set temperature, and is stabilized.

According to the eighth invention or twenty-first invention, by flowing a fluid at a predetermined temperature so as to contact with or come close to the temperature controlling region, since temperature controlling of the temperature controlling region can be performed from far distance, it is not necessary to provide the temperature raising and lowering body or the constant temperature source so as to be near or come close to the nozzle, a space in vicinity of the nozzle can be utilized in other treatment such as measurement or the like, a utilization efficiency of a space is high.

According to the ninth aspect of the invention, since a fluid can be concentrated, without loss, into the temperature controlling region in which a liquid to be temperature-controlled is situated, an efficiency is high, and since the temperature controlling region is surrounded from the outside of a temperature regulating chamber, uniform temperature controlling having high reliance can be performed.

According to the tenth or twenty-second aspect of the invention, by providing the temperature controlling region of the nozzle relatively movably to the temperature raising and lowering body, the constant temperature source or the fluid source, temperature controlling can be replaced by transfer controlling, thereby, transfer of a liquid and temperature controlling can be handled at the same level, and centrifugation of controlling and higher efficiency of treatment can be contacted. In addition, since it is enough to make a member for temperature controlling approach the nozzle only when temperature controlling is performed, a utilization efficiency of a space in vicinity of the nozzle is high.

According to the eleventh or twenty-third aspect of the invention, since by measuring light emission in the temperature controlling region of the nozzle, light emission regarding only a liquid whose temperature controlling has been performed can be measured, light emission satisfying temperature controlling purpose can be assuredly measured. In addition, temperature controlling of a liquid and measurement of light emission can be consistently automated using the same apparatus.

According to the twelfth aspect of the invention, since by choking the interior of the nozzle, particularly, the temperature controlling region openably and closably to the outside using the nozzle choking member upon temperature controlling, liquid leakage from a tip of the nozzle due to inflation of a liquid upon temperature controlling can be assuredly prevented, cross contamination can be prevented, and high reliance temperature controlling can be performed.

According to the thirteenth or twenty-fifth aspect of the invention, a liquid to be temperature-controlled is sealed in the nozzle by holding it with a sealing liquid in the nozzle from up and down. For this reason, since the liquid can be sealed without contact with the air, mixing of the bubbles into a liquid can be assuredly prevented, therefore, temperature controlling having high reliance can be performed. In addition, since a liquid to be temperature-controlled can be set at a liquid amount smaller than a liquid amount corresponding to the temperature controlling region in the nozzle, a time of temperature controlling is shortened, and a focal point in the case of light measurement can be adjusted.

According to the fourteenth aspect of the invention, by providing a movable cap or a fixed cap, with simple construction, treatment of choking the nozzle can be replaced with controlling of transfer of the nozzle, therefore, treatment can be simplified, and rapid and effective pressurizing treatment can be performed. Particularly, in the case of a movable cap, falling is possible due to inflation of a gas, but in the case of the fixed cap, there is not a possibility of falling.

According to the fifteenth aspect of the invention, by sucking a liquid amount to an extent exceeding the temperature controlling region, and adjusting a position so as to come out from the temperature controlling region up and down, mixing of the air into the temperature controlling region can be prevented, and influence of temperature controlling on the air present above and below the liquid can be made to be small, therefore, foaming in the temperature controlling region can be arrested, and inflation of the gas outside the temperature controlling region due to temperature controlling can be avoided.

According to the twenty-sixth aspect of the invention, by discharging a liquid accommodated in the nozzle into the container, since a liquid which has been temperature-controlled can be continuously further treated, diverse and general-use treatment can be performed.

According to the twenty-seventh aspect of the invention, by coloring of any of a sucked liquid, since a position of the liquid can be assuredly captured with a photosensor, positional adjustment of high reliance can be assuredly and easily performed.

According to the twenty-eighth aspect of the invention, since the choking member for choking the small-diameter openably and closably is provided below the temperature-controlling region, a liquid to be temperature-controlled can be assuredly pressurized in the disposable tip by assuredly choking the nozzle using the choking member. Thereby, foaming of a liquid can be prevented, and treatment of high reliance can be performed.

According to the twenty-ninth aspect of the invention, by providing an on-off valve which can be opened and closed by remote operation with a magnetic force from the outside as the choking member, since opening and closing operation can be performing without contacting with the nozzle, contamination of the nozzle can be prevented. In addition, since the valve can choke the nozzle firmer by pressurizing, it can assuredly choke the nozzle.

According to the thirteenth or thirty-first aspect of the invention, by fixing a plurality of substances to be temperature-controlled on, a plurality of respective particle-like carriers or an aggregate of a plurality of sets of respective particle-like carriers, temperature control of a plurality of subjects can be performed assuredly and parallel. Particularly, the invention is effective when a substance to be temperature-controlled is a nucleic acid or the like, and temperature controlling is based on the PCR method. Thereby, temperature controlling of a plurality of subjects can be effectively performed under the generally same condition.

BEST MODE FOR CARRYING OUT THE INVENTION

Figure 1:
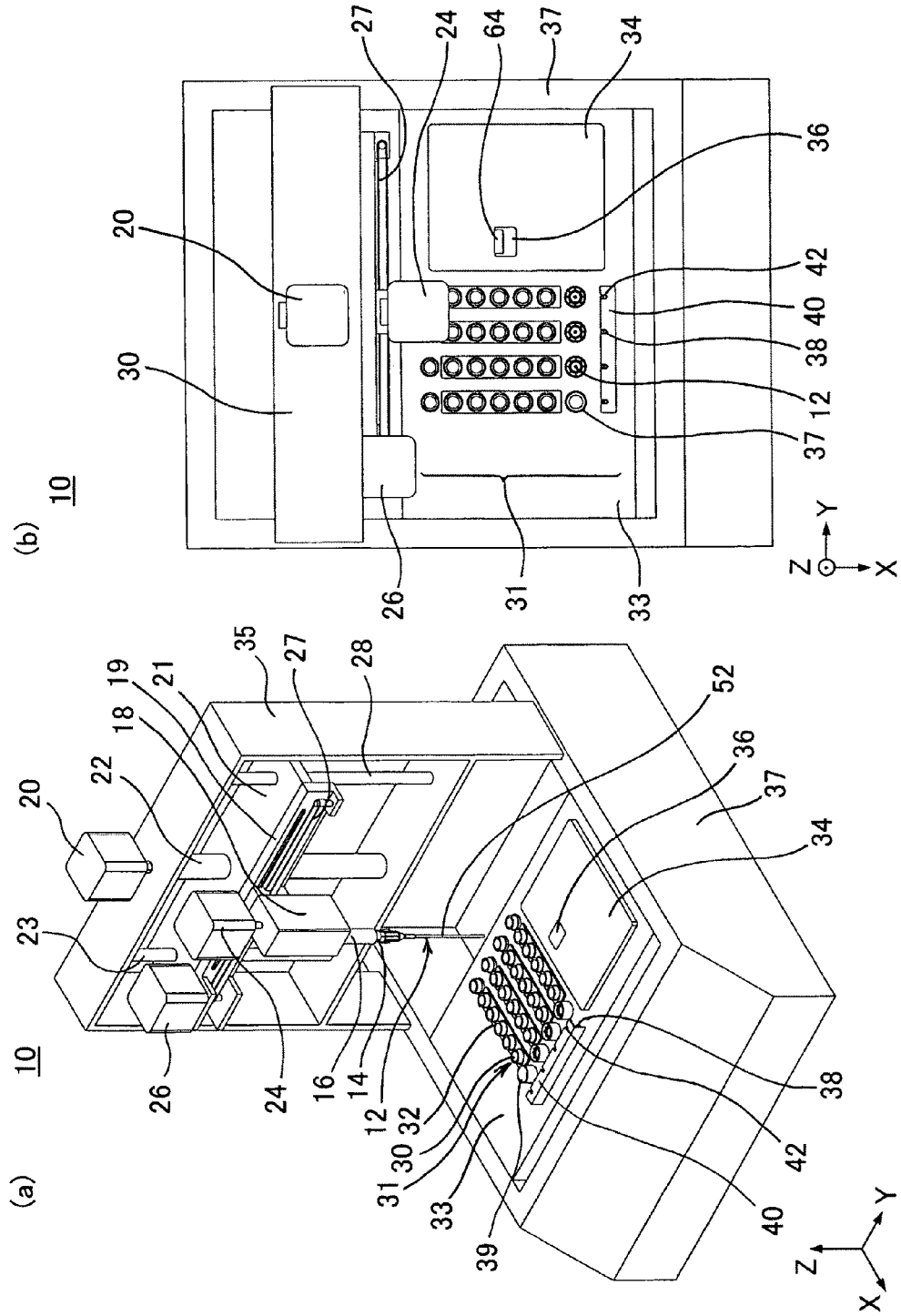
FIG. 1 is a perspective and a plane view showing a whole of the temperature controlling apparatus of the first embodiment.

FIG. 1 is a perspective or a plane view showing a whole of a temperature controlling apparatus 10 of the first embodiment.

The present temperature controlling apparatus 10 is an apparatus for performing temperature controlling necessary for a predetermined liquid by repeating maintenance of the liquid at a set temperature for a set time, it includes a disposable tip 12 which sucks the liquid to be temperature-controlled into the inside, and discharges a liquid which has been temperature-controlled, and a mounting nozzle 14 in which the disposable tip 12 is mounted, and has a suction and discharge mechanism of performing suction and discharge of a gas via the mounting nozzle 14, a container group 31 for containing the liquid to be temperature-controlled and accommodating various liquids, a regulation measurement part for performing temperature regulation and light measurement, and a movement mechanism for relative movement between the disposable tip 12, and the container group 31 and the regulation measurement part.

The suction and discharge mechanism has a mounting nozzle 14 in which the disposable tip 12 is to be mounted, a cylinder communicating with the mounting nozzle 14 and a plunger sliding in the cylinder, a nut part connected to the plunger for driving the plunger up and down, a nozzle head 18 which is engaged with the nut part threadly, and accommodates a ball screw which moves the nut part up and down by rotation, and a P axial motor 24 which rotates and drives the ball screw.

In addition, the apparatus has a detachment cylinder 16 provided with a hollow part having such a size of internal diameter that the mounting nozzle 14 can pass, but the mounted disposable tip 12 cannot pass, as the detachment member, above the disposable tip 12 and the mounting nozzle 14. The detachment cylinder 16 is provided movably up and down along an axial direction concentrically with the mounting nozzle 14 and the disposable tip 12. Before implementation of detachment of the detachment cylinder 16, in the interior of the hollow part, a flow tube described later communicating between a rear end of the mounting nozzle 14, the mounting nozzle 14 and the cylinder is situated.

The container group 31 is provided on a stage 33, and is such that container rows in which four kinds of liquids to be temperature-controlled, for example, six containers including specimens of four persons, a container accommodating a relevant reagent used in treatment of its one kind liquid, a vacant container accommodating a product and the like are arranged in an X-axial direction are arranged in four rows in corresponding a Y-axial direction for every four kinds of liquids to arrange 6 columns×4 rows matrix as a whole. The each container row has, in addition to a container 30 accommodating the liquids to be temperature-controlled, a container 32 accommodating a sealing liquid described later, a container accommodating other necessary various reagent solutions, for example, a primer, a reverse primer, a modified primer (e.g. a biotinylated primer, a fluorescently labeled primer), four kinds of bases, a DNA synthetase and the like, various buffers, or a washing solution, or a vacant container accommodating the liquid which has been temperature-controlled.

In addition, in the container group 31, corresponding to the container row of four kinds of liquids, four tip accommodating parts 39 in which the vacant disposable tip 12 used regarding the liquid is accommodated with a mounting opening described later on an upper side are arranged, by one column, at a position corresponding to each container row at a row interval between container rows for every each liquid. In addition, the tip accommodating part 39 in which the mounted disposable tip 12 is accommodated is vacant now.

In the container group 31, a movable cap 38 which is to be mounted at a tip of the disposable tip 12 is set and provided, by one column, at a position having a row interval corresponding to the each container row for every each liquid. Above the movable cap column, a small-diameter tube 52 of the disposable tip 12 can pass with the row interval so as to correspond to each arrangement position of the movable cap 38, and a U-shaped notch part 42 having such a width that the movable cap 38 cannot pass while the cap is mounted at a tip of the disposable tip 12 is arranged on a cap detachment horizontal plate 40 which is formed along a Y-axial direction so as to cover the movable cap 38.

On the stage 33, further, a dark box 34 for shielding light from the outside for performing temperature controlling and light measurement is provided. In the dark box 34, a device corresponding to the regulation measurement part is provided. In the dark box 34, an insertion pore 36 in which the disposable tip 12 can be inserted is provided, and the box has such a depth that a full length of the disposable tip 12 can be accommodated.

Then, as the movement mechanism, there are a Z axial movement mechanism for moving the disposable tip 12 mounted in the mounting nozzle 14, in a Z-axial direction on the drawing, a Y-axial movement mechanism for movement in a Y-axial direction, and a X-axial movement mechanism for movement in a X-axial direction.

The Y-axial movement mechanism has a Y-axis guide member 19 which is provided along a Y-axial direction, and supports the nozzle head 18 movably, a timing belt 27 which is engaged with a pulley provided in the nozzle head 18, and a Y-axial motor 26 which is provided in the Y-axis guide member 19 and runs the timing belt 27.

In addition, the Z-axial movement mechanism has a X-axial moving plate 21 which is connected with the Y-axis guide member 19, and can be moved along a Z-axial direction by guided by two guide posts 23, 28, a Z-axial ball screw 22 with which a nut part provided in the Z-axial movement plate 21 is threaded, and a Z-axial motor 20 which rotates and drives the Z-axial ball screw 22.

The Z-axial motor 20, the guide posts 23, 28 and the Z-axial ball screw 22 are supported by a frame 35 fixed on a box-like substrate 37.

In addition, as the X-axial movement mechanism, there is a mechanism (not shown) which can move the stage 33 to the X-axial direction relative to the substrate 37, therefore, relative to the frame 35, and the disposable tip 12, for example, a mechanism using a ball screw or a timing belt.

In addition, as the controlling part, the information processing apparatus (not shown) having a peripheral device including an inputting device such as CPU, a key board, a switch, a mouse, a communication device, a display device such as a liquid crystal panel, or an outputting device such as CD, a DVD driver, a printer for performing instructions of a liquid to be sucked in the nozzle and a liquid amount thereof, adjustment of a position of the sucked liquid in the nozzle, and temperature controlling, to the movement mechanism, the sucking and discharge mechanism and the temperature regulator, or instructions of choking to the movement mechanism, or pressurization to the sucking and discharging mechanism is provided in the temperature controlling apparatus 10. By the inputting device, designation of a container for accommodating a liquid to be temperature-controlled by a user, designation of its liquid amount, setting of one or two or more temperatures, setting of its maintenance time, setting of its order, and setting of a cycle number and a cycle time are performed and, based on the input, an instruction signal is output to the movement mechanism by program controlling which has been pre-introduced into the information processing device.

Figure 2:
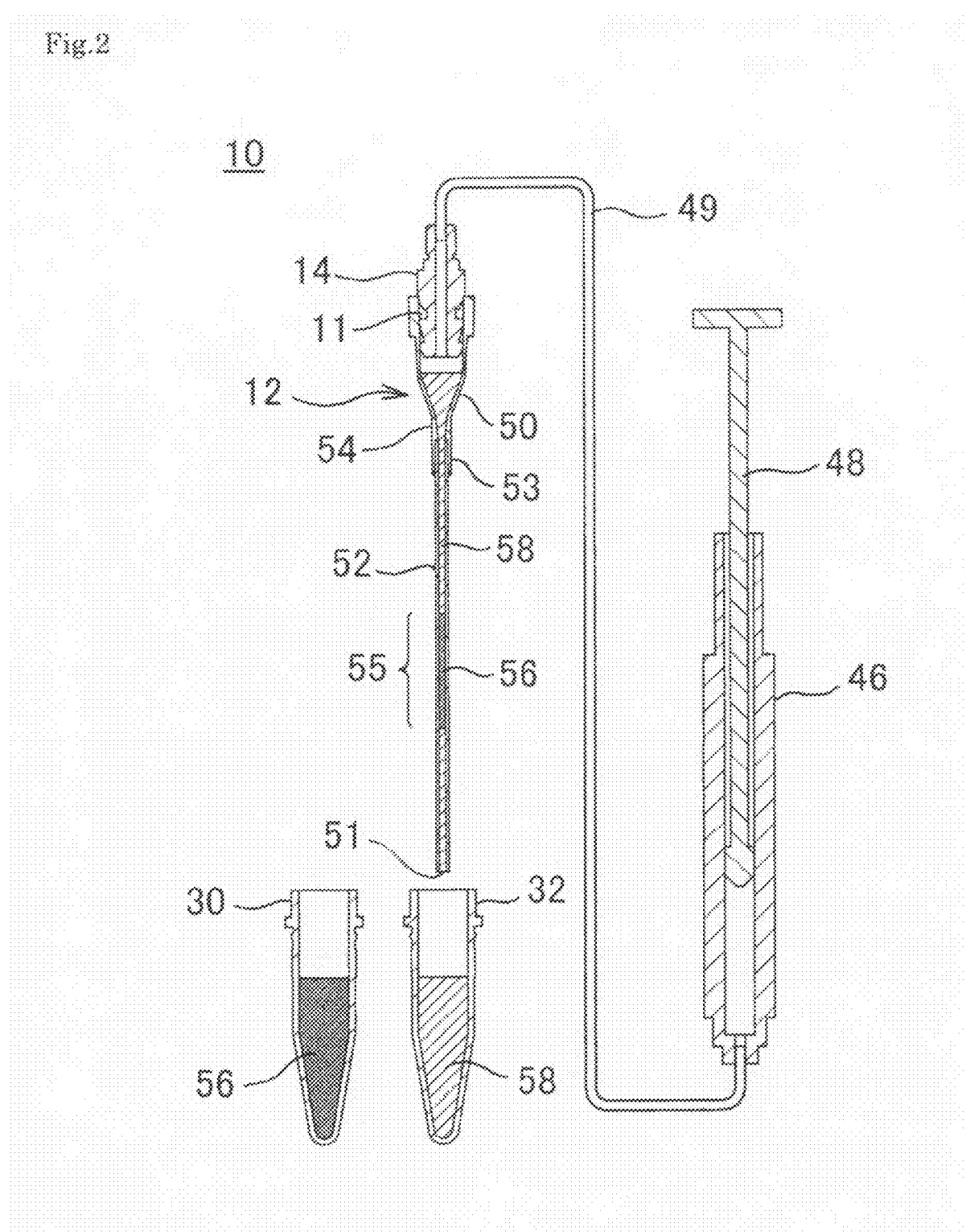
FIG. 2 is a cross-sectional view showing an example at suction of the temperature controlling apparatus of the first embodiment.

FIG. 2 shows enlargement of a main part of the temperature controlling apparatus 10 of the first embodiment of the present invention and, at the same time, explains motion of suction of a liquid to be temperature-controlled.

Among the temperature controlling apparatus 10, the mounting nozzle 14, the disposable tip 12 mounted in the mounting nozzle 14, a suction and discharge mechanism, and containers 30, 32 of the container group 31 are extracted and shown. The mounting nozzle 14 is communicated with a cylinder 46 via a flow-tube 49, and the flow-tube 49 is provided in a hollow part of the detachment cylinder 16 shown in FIG. 1. before implementation of detachment In the disposable tip 12, the mounting opening 11 is fitted and mounted at a lower end of the mounting nozzle 14. The mounting nozzle 14 is communicated with the cylinder 46 via a flow-tube 49, and a plunger 48 is slidably provided in the cylinder 46. The mounting nozzle 14, the flow-tube 49, the cylinder 46, and the plunger 48 constitute the suction and discharge mechanism which can suck and discharge a gas via the mounting nozzle 14.

The disposable tip 12 has a large-diameter tube 50 on which the mounting opening 11 is provided, a small-diameter tube 52 which is formed to be thinner than the large-diameter tube 50, and in which a liquid can be flowed into and out of a tip thereof, and a funnel-like transition part 54 which is formed between the large-diameter tube 50 and the small-diameter tube 52. On a lower side of the transition part 54, an upper end of the small-diameter tube 52 is fitted, and a fitting end 53 attached by ultrasound welding, thermal welding or an adhesive is possessed. An internal diameter of the small-diameter tube 52 and an internal diameter of the transition part 54 are smoothly connected.

The small-diameter tube 52 has a straight axis, and an internal diameter having herein a size of, for example, 1 mm is constant over a full length (e.g. about 70 mm) along its axial direction. Thereby, controlling of a position of a liquid and controlling of a temperature are easily performed.

In the small-diameter tube 52, one temperature controlling region 55 is set and, in the temperature controlling region 55 one or two or more set temperatures are maintained for each predetermined time with a temperature regulator described later, in a predetermined order, in a predetermined cycle time, and by the determined cycle numbers.

Figure 3:
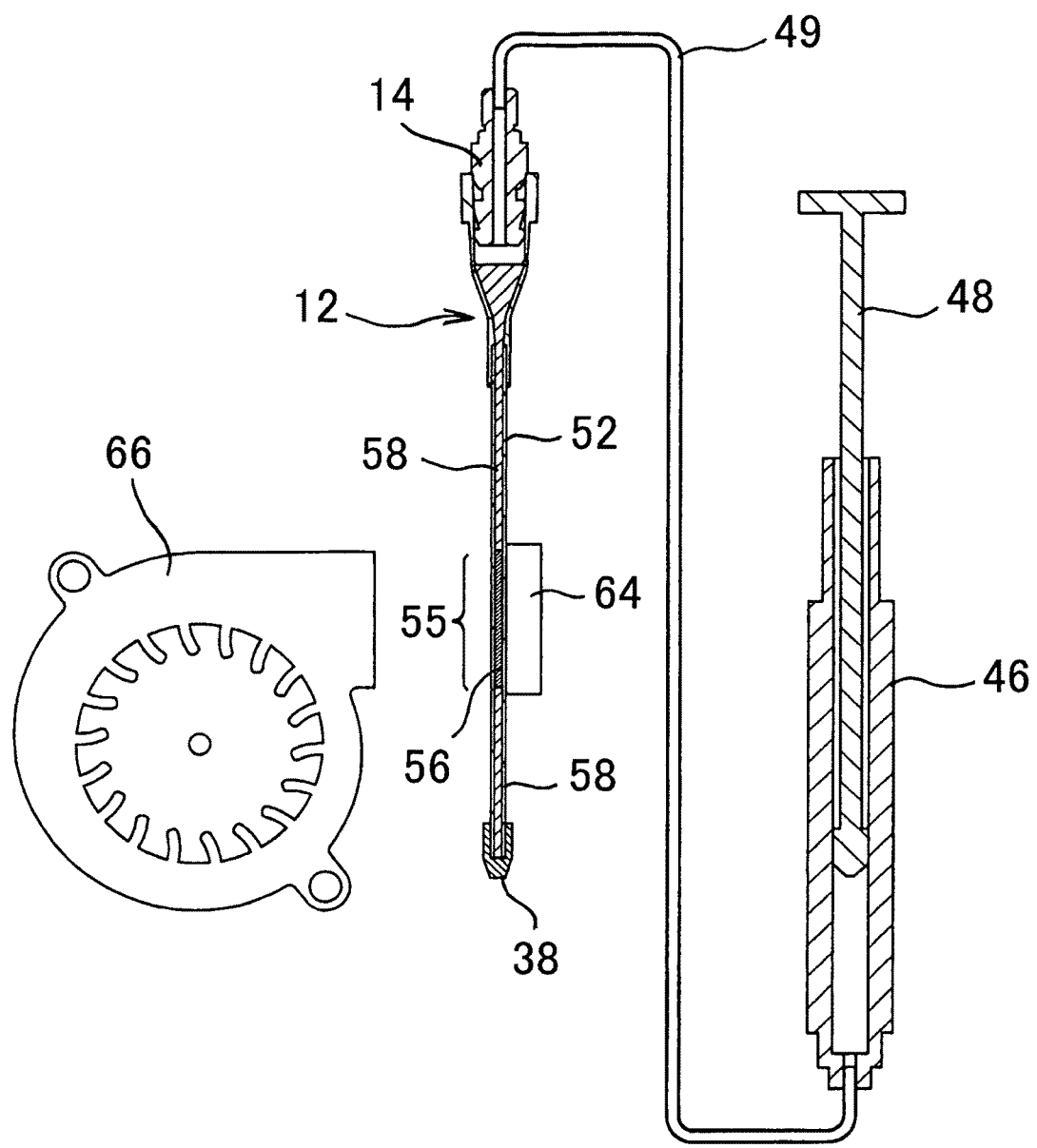
FIG. 3 is a cross-sectional view showing an example at temperature controlling of the temperature controlling apparatus of the first embodiment.

FIG. 3 shows the state where after the movable cap 38 is fitted and mounted in a tip of the disposable tip 12, a temperature raising and lowering body 64 having a Peltier element as a temperature regulator is contacted with the temperature controlling region 55, or the case where a fan 66 as a temperature regulator is situated at the small-diameter tube 52 of the temperature controlling region 55, and the disposable tip 12 is situated at a location at which an air stream as a fluid is ejected.

Subsequently, based on FIG. 1 to FIG. 3, a procedure for performing temperature controlling and light measuring regarding a liquid to be temperature-controlled will be explained.

After the nozzle head 18 is moved to above the tip accommodating part 39 using the X-axial movement mechanism and the Y-axial movement mechanism, the mounting nozzle 14 is lowered using the Z-axial movement mechanism to insert its tip into the mounting opening 11 of the accommodated disposable tip 12 to perform fitting and mounting. Thereafter, the nozzle head 18 is lifted to completely extract the disposable tip 12 from the tip accommodating part 39.

Then, the disposable tip 12 is moved to above the container 32 in which an oily sealing liquid 58 is accommodated, using the X-axial moving mechanism. Then, using the Z-axial movement mechanism, a mouth part 51 at a tip of the small-diameter tube 52 of the disposable tip 12 is inserted into the container 32, a predetermined amount of the sealing liquid 58 is sucked and, thereafter, the mouth part 51 of the disposable tip 12 is extracted from the container 32 using the Z-axial movement mechanism.

Subsequently, the disposable tip 12 is moved to the container 30 using the X-axial movement mechanism, the mouth part 51 is inserted into the container 30, a liquid 56 to be temperature-controlled is sucked, and after a tip part of the disposable tip 12 is extracted from the container 30, again, the disposable tip 12 is returned to the container 32, the mouth part 51 at a tip of the small-diameter tube 52 is inserted into the container 32, the sealing liquid 58 is sucked, and the liquid 56 to be temperature-controlled is held with the sealing liquid 58 from upper and lower directions.

Next, after the disposable tip 12 is moved to above the movable cap 38 using the X-axial movement mechanism, the tip is lowered through the U-shaped notch part 42 using the Z-axial movement mechanism, a tip of the disposable tip 12 is inserted into the movable cap 38 to fit and mount it therein. Thereupon, it is preferable that choking is performed so that the air is not introduced below the temperature controlling region of the disposable tip 12. After the disposable tip 12 mounted with the movable cap 38 is lifted slightly using the Z-axial movement mechanism, the disposable tip 12 is moved using the X-axial movement mechanism in a X-axial direction, thereby, the small-diameter tube 52 of the disposable tip 12 is detached from the U-shaped notch part 42, thereafter, the movable cap 38 mounted at a tip of the disposable tip 12 is positioned at a location higher than a height of the cap detaching horizontal plate 40 using the Z-axial movement mechanism.

Next, the disposable tip 12 is moved to a position above an insertion pore 36 of the dark box 34 using the X-axial movement mechanism and Y-axial movement mechanism. Then, the disposable tip 12 is lowered through the insertion pore 36 using the Z-axial movement mechanism to accommodate a whole of the disposable tip 12 in the dark box 34.

Thereupon, a degree of lowering of the disposable tip 12 is determined so that the temperature controlling region 55 of the disposable tip 12 is positioned at the temperature raising and lowering body 64 provided in the dark box 34. At this position, the controlling part instructs the suction and discharge mechanism to pressurize the interior of the disposable tip 12 at a predetermined pressure in the state where the mouth part 51 is choked with the movable cap 38. A magnitude of this pressuring is, for example, a magnitude to such a degree that foaming of the air dissolved in a liquid can be suppressed. Alternatively, a pressure depending on each predetermined temperature set by temperature controlling may be applied.

Figure 13:
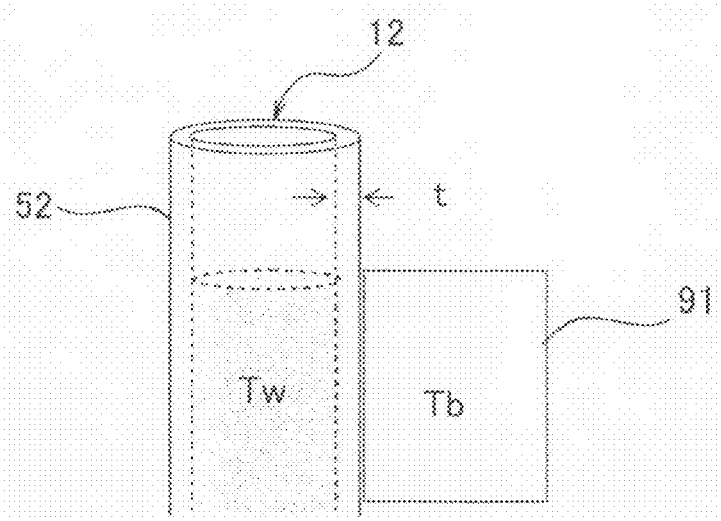
FIG. 13 is an experimental view showing following capability of a temperature of the nozzle used in the temperature controlling apparatus of the first embodiment.
Figure 13:
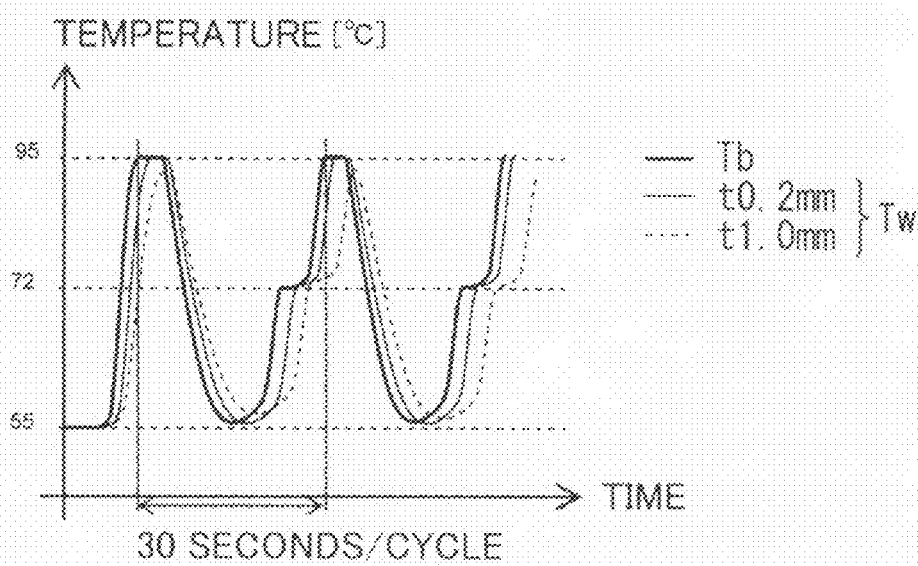

The temperature raising and lowering body 64 performs temperature controlling by repeating predetermined cycle numbers in a predetermined order within a predetermined cycle time while two or more predetermined temperatures are maintained for predetermined two or more respective predetermined times. Thereupon, light emission in the temperature controlling region 55 is measured with the light measuring equipment in the dark box 34. For example, as shown in FIG. 13, in order to maintain 94° C. as a predetermined temperature for 5 seconds, 50° C. for 5 seconds, and 74° C. for 10 seconds so that one cycle as a whole is within 30 seconds, when a temperature is transferred from 94° C. to 50° C., for example, cooling is performed for a predetermined time (transfer time) at 25° C. as the transfer promoting temperature.

Further, when a liquid which has been temperature-controlled is utilized by discharging from the disposable tip 12, the disposable tip 12 which has been temperature-controlled is extracted from the dark box 34 through the insertion pore 36 using the Z-axial movement mechanism, and the small-diameter tube 52 of the disposable tip 12 is positioned so as to be inserted into the U-shaped notch part 42, using the X-axial movement mechanism and Y-axial movement mechanism, so that the movable cap 38 comes below the cap detachment horizontal plate 40. Next, by moving the disposable tip 12 upwardly using the Z-axial movement mechanism, it is engaged with the movable cap 38 which cannot pass through the U-shaped notch part 42, the movable cap 38 is detached from a tip of the disposable tip 12.

This is performed by moving the disposable tip 12 from which the movable cap 38 has been detached to above the corresponding container of the container group 31 using the X-axial movement mechanism and the Y-axial movement mechanism, inserting a tip of the disposable tip 12 into the container using the Z-axial movement mechanism, discharging the lower side sealing liquid among a liquid retained in the interior, and moving the disposable tip 12 to a vacant container for accommodating a product to discharge the temperature-controlled liquid into the container. If necessary, the disposable tip 12 is moved to a container from which the lower side sealing liquid has been discharged, to discharge an upper sealing liquid.

In addition, when there are a plurality of kinds of liquids to be temperature-controlled, treatment of one liquid is completed, a liquid of the disposable tip 12 is completely discharged, the disposable tip 12 is moved to above the tip accommodating part 39 which has accommodated it using the X-axial movement mechanism and the Y-axial movement mechanism, the disposable tip 12 is inserted into the tip accommodating part 39 using the Z-axial movement mechanism, and the detachment cylinder 16 is lowered along an axial direction of the mounting nozzle 14, thereby, the mounted disposable tip 12 is detached. Thereafter, mounting is performed from the tip accommodating part in which a new disposable tip 12 is accommodated as described above and treatment is initiated.

Figure 4:
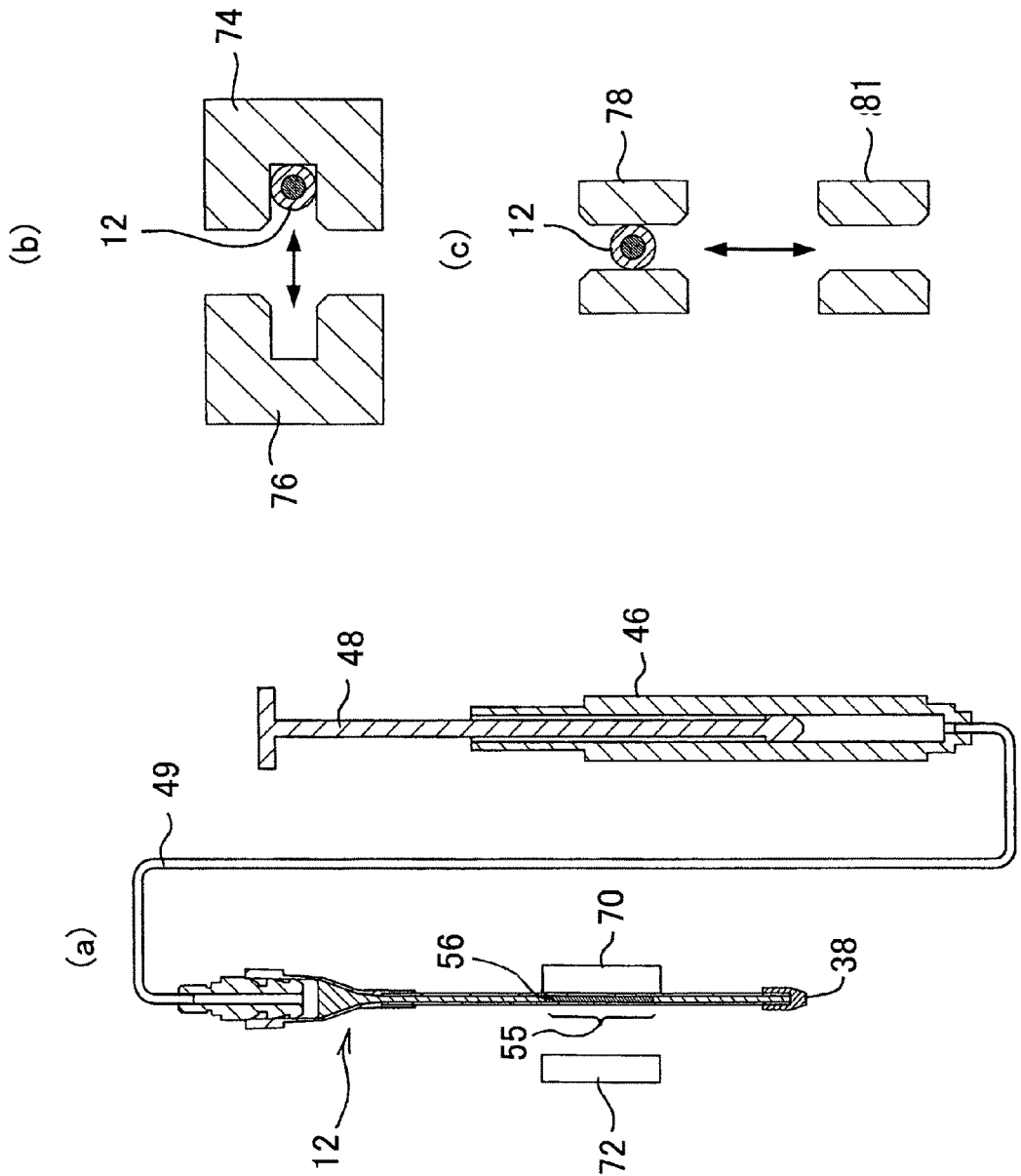
FIG. 4 is a cross-sectional view showing other example at temperature controlling of the temperature controlling apparatus of the first embodiment.

FIG. 4(A) shows the case where a constant temperature source 70 which is accessibly and departably provided in the disposable tip 12 and is set at a predetermined temperature, as a temperature regulator, comes close to and is contacted with the temperature controlling region 55 of the disposable tip 12, and other constant temperature source 72 set at a predetermined temperature different from the predetermined temperature is departed. Therefore, the temperature controlling region 55 is retained at a temperature set by the constant temperature source 70. After contacted with the constant temperature source 70 for a constant time, the constant temperature source 70 is departed, the constant temperature source 72 is made to come close to and contact, and a temperature becomes to be retained at a temperature set by the constant temperature source 72. Thereafter, the state where moved to a position at which the constant temperature source 72 is provided, is shown.

FIG. 4(B) shows constant temperature sources 74, 76 of other example. Since the constant temperature sources 74, 76 are provided so as to surround the disposable tip 12 from three directions, uniform temperature controlling can be performed on the temperature controlling region 55.

FIG. 4(C) shows constant temperature sources 78, 81 as a temperature regulator of a further other example. Since the constant sources 78, 81 are provided so as to hold the disposable tip 12, the sources can be easily moved to the temperature controlling region 55, and temperature controlling can be effectively performed.

Figure 5:
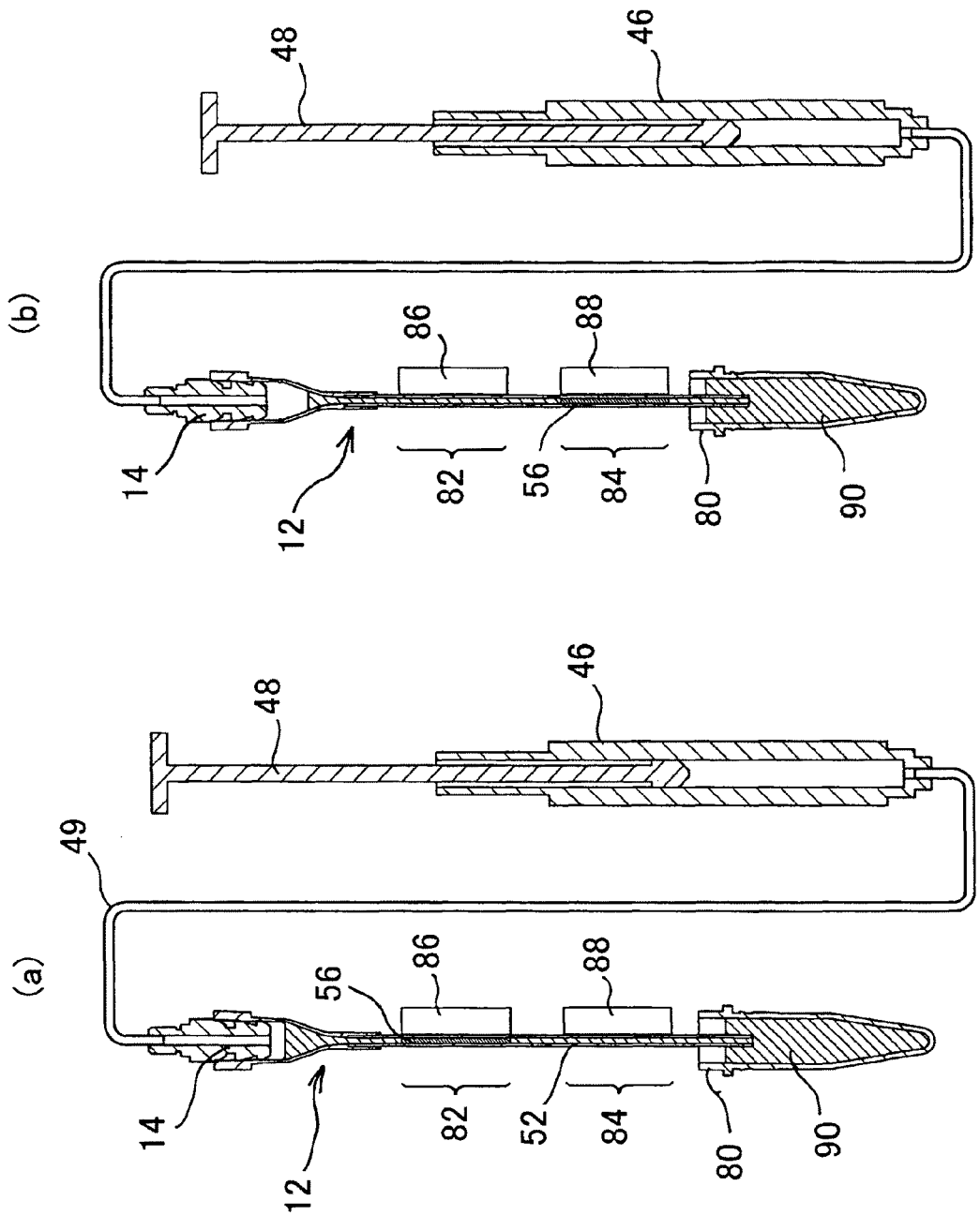
FIG. 5 is a cross-sectional view showing other example at temperature controlling of the temperature controlling apparatus of the first embodiment.

In FIG. 5, in the small-diameter tube 52 of the disposable tip 12, two temperature controlling regions 82, 84 are provided so as to be departed from each other. With respect to respective temperature controlling regions 82, 84, two temperature raising and lowering bodies 86, 88 which can be maintained at respective set one or two or more predetermined temperatures are provided in respective temperature controlling regions 82, 84. FIG. 5(A) shows a sucked liquid 56 to be temperature-controlled, which is held in up and down directions with a seeling liquid 90 sucked from a container 80, in FIG. 5(A), this is positioned at an upper side temperature controlling region 82 and, in FIG. 5(B), a sucked liquid 56 to be temperature-controlled is positioned at a lower side temperature controlling region 84.

Figure 6:
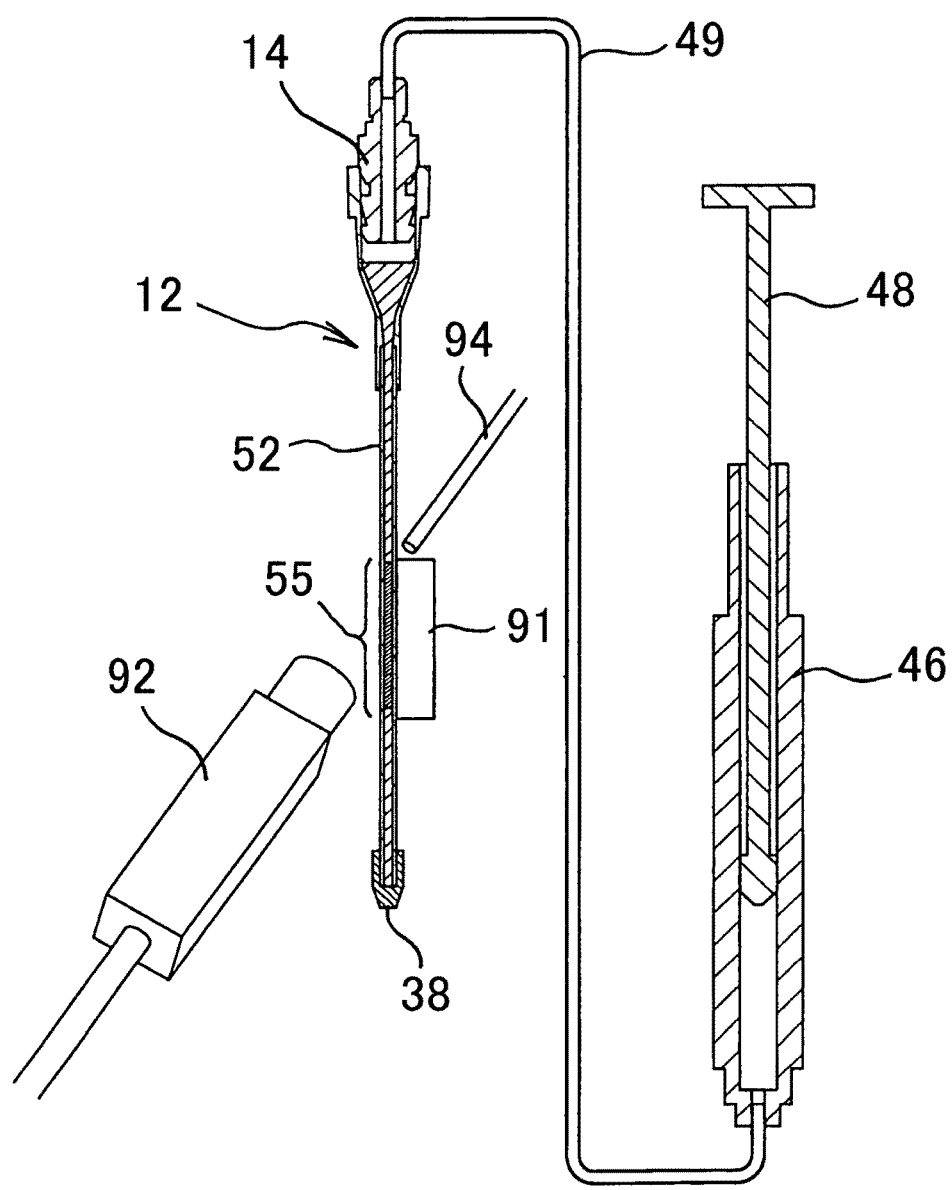
FIG. 6 is a cross-sectional view showing an example at light measurement of the temperature controlling apparatus of the first embodiment.

In FIG. 6, in the temperature controlling region 55 set in the small-diameter tube 52 of the disposable tip 12, as the temperature regulator, a temperature raising and lowering body 91 is contacted and, at the same time, as an irradiation part, a trigger light source 92 for irradiating trigger light for exciting a fluorescent substance, and a light receiving optical fiber 94 as a light receiving end for receiving emitted light of a fluorescent substance are provided so as to hold the temperature controlling region 55.

Figure 7:
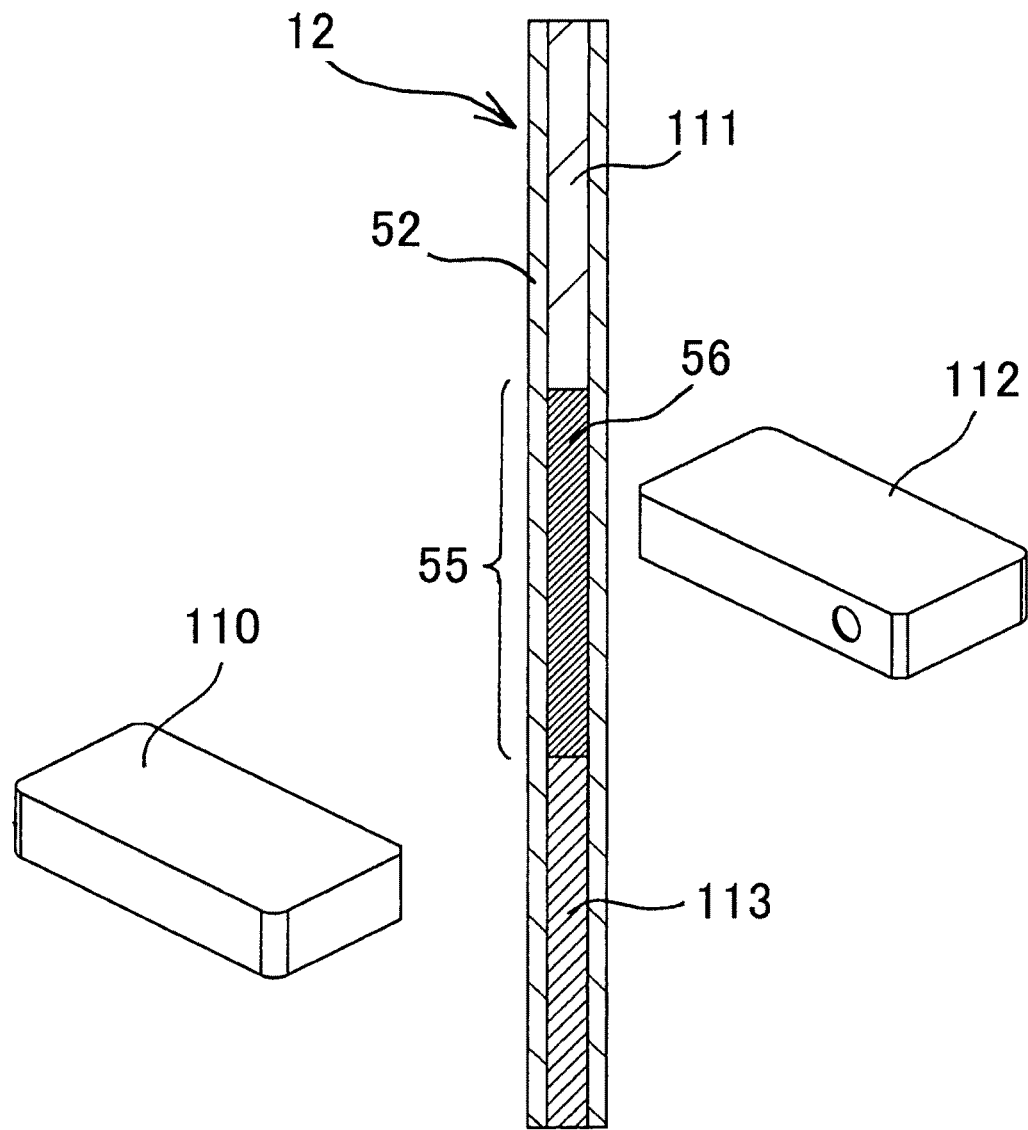
FIG. 7 is a partially cross-sectional perspective showing an example at adjustment of a position of a liquid of the temperature controlling apparatus of the first embodiment.

FIG. 7 shows a light transmittance sensor light emitting part 110, and a photosensor light receiving part 112 arranged so as to receive light from the light transmittance sensor light emitting part 110 through the temperature controlling region 55, which are provided facing each other holding the temperature controlling region 55 provided in the small-diameter tube 52 of the disposable tip 12. They are used for detecting whether a liquid 56 has reached a position of a temperature controlling region when a position of the liquid 56 to be temperature-controlled is adjusted. When the liquid 56 is present, since transmittance of a light by light emission from the light transmittance sensor light emitting part 110 is prevented, the photosensor light receiving part 112 cannot receive a constant light amount and, therefore, whether the liquid 56 is maintained in the temperature controlling region 55 or not can be measured.

Alternatively, not the liquid 56, but a substance which prevents such the transmittance of light may be contained in one of sealing liquids 111, 113 or both of them. In this case, an upper side sealing liquid 111 and a lower side sealing liquid 113 show different cases. In addition, it is preferable that the light transmittance sensor light emitting part 110 and the photosensor light receiving part 112 are provided in the dark box 34 in which temperature controlling is performed.

Figure 8:
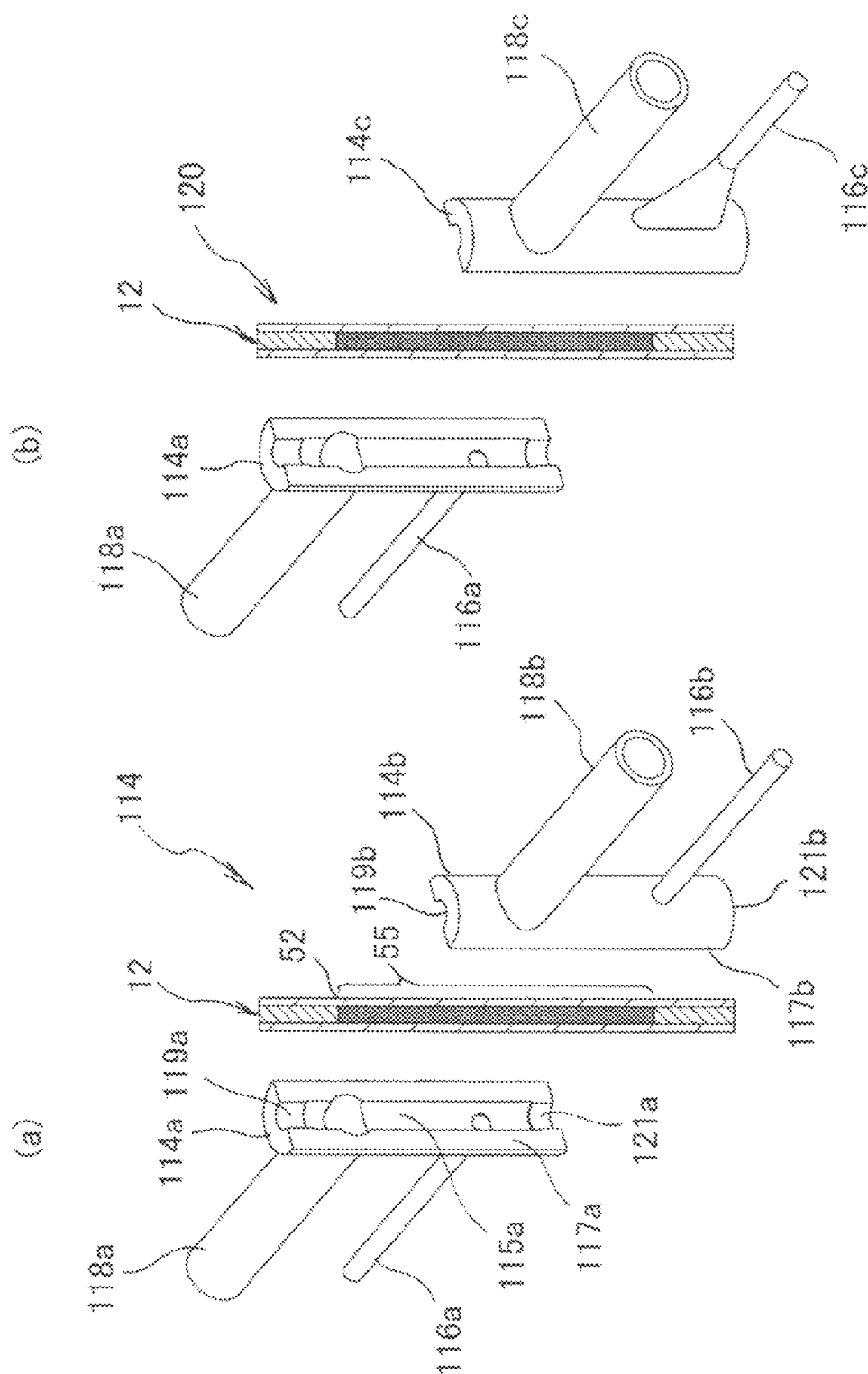
FIG. 8 is a partially cross-sectional perspective showing an example at temperature controlling and a light measurement of the temperature controlling apparatus of the first embodiment.

FIG. 8 shows an exploded perspective of cylindrical support connecting tubes 114, 120 through which a fluid surrounding the temperature controlling region 55 can pass, for supporting an irradiation end and the light receiving end of light measuring means in the temperature controlling region 55 of the small-diameter tube 52 of the disposable tip 12, and contacting a fluid sent from a temperature regulator with the temperature controlling region 55. The support connecting tube 114 corresponds to the temperature regulation chamber having the interior through which the small-diameter tube 52 of the disposable tip 12 penetrates, is used for connecting semi-cylindrical support connecting half-tube 114a, 114b corresponding to a division temperature regulation chamber and, in the support connecting half-tube 114a, an irradiation optical fiber 116a as an irradiation end of the light measuring means, and an upstream tube 118a through which a fluid (gas or liquid) set at a predetermined temperature sent from a temperature regulator is flowed, are provided, protruding in a radial direction. On the other hand, in the support connecting half-tube 114b, a light receiving optical fiber 116b as a light receiving end of the light measuring means, and a downstream tube 118b for discharging a fluid from the upstream tube 118a are provided, protruding in a radial direction. The fluid may be circulated.

The support connecting half-tubes 114a, 114b can closely contacted with an external circumferential surface of the small-diameter tube 52, and has internal circumferential edge faces 119a, 121a, 119b and 121b provided on both ends of the support connecting tube 114, internal circumferential intermediate surfaces 115a, 115b which have a greater diameter than an external circumferential surface of the small-diameter tube 52, and are held by the internal circumferential edge face, and joining surfaces 117a, 117b. By inscribing to half-cylindrical support connecting half-tubes 114a, 114b against an external circumferential surface of the small-diameter tube 52 with the internal circumferential edge surfaces 119a, 121a, 119b 121b, and closely contacting them with the joining surfaces 117a, 117b, they are attached to the small-diameter tube 52. The fluid is flowed in a cavity generated in the interior while contacting with a side surface of the temperature controlling region 55.

Similarly, in the support connecting tube 120, the situation is the same, but in the support connecting half-tube 114c, on an internal circumferential intermediate surface of the support connecting half-tube 114c, unlike the light receiving optical fiber 116b of the support connecting half-tube 114b, the light receiving optical fiber 116c having an end formed so as to develop towards the temperature controlling region 55 so that light is easily collected is provided. These support connecting tubes 114, 120 are provided below the insertion pore 36 of the dark box 34, and is attached to the small-diameter tube 52 of the disposable tip 12 with a mechanism placing each other in a nozzle direction so as to hold the nozzle. The support connecting tube may be formed so that it is provided in the state where it has been connected to the small-diameter tube 52 of the disposable tip 12 in advance. In this case, the support connecting tube is moved with a nozzle head.

Figure 9:
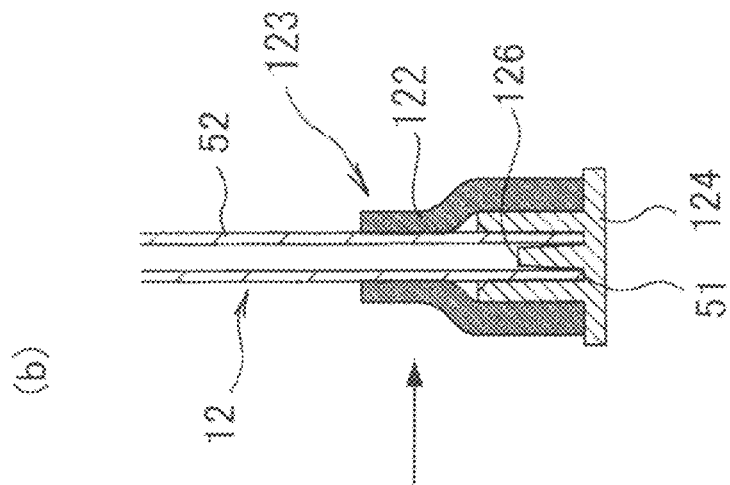
FIG. 9 is a cross-sectional view showing an example at temperature controlling of the temperature controlling apparatus of the first embodiment.
Figure 9:
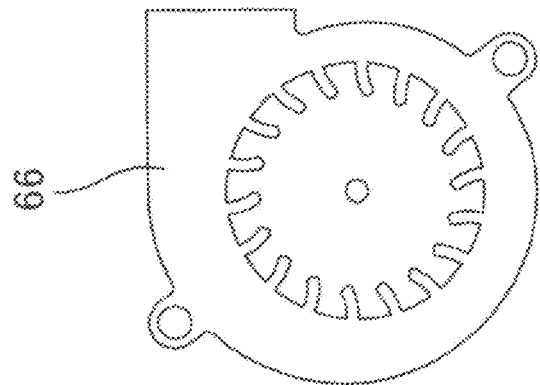
Figure 9:
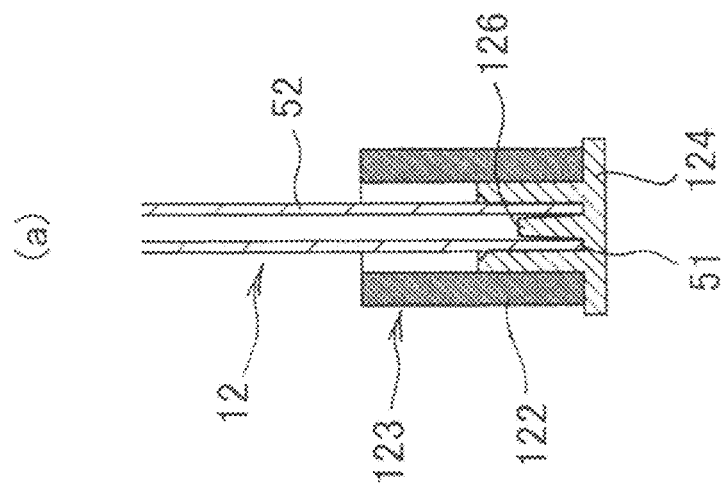
Figure 10:
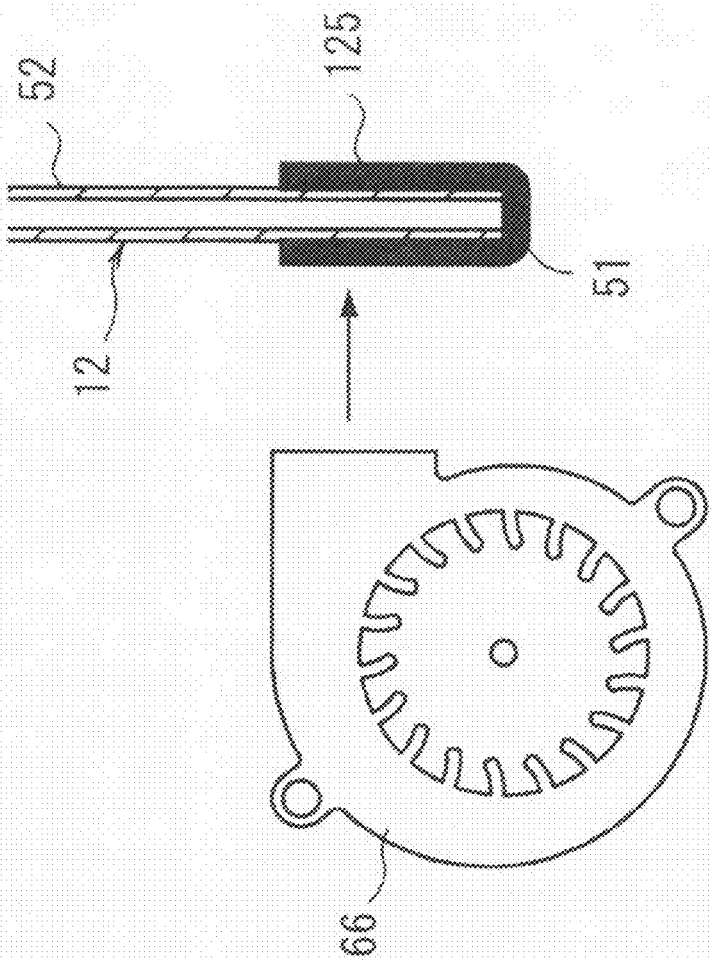
FIG. 10 is a cross-sectional view showing other example at temperature controlling of the temperature controlling apparatus of the first embodiment.
Figure 10:
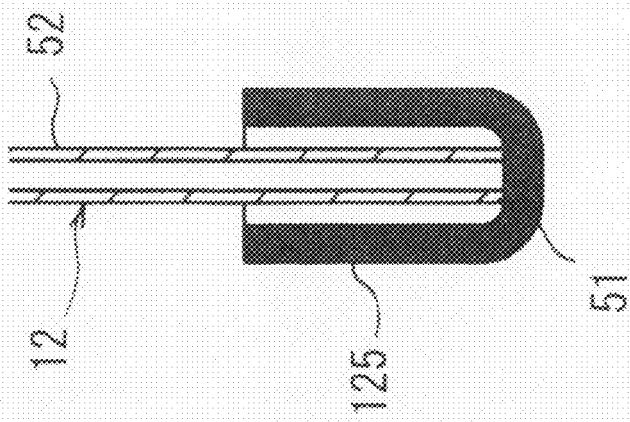

FIG. 9 and FIG. 10 show cases where the fixed cap 123 and the movable cap 125 as the nozzle choking member which are provided outside the disposable tip 12, and can choke the disposable tip 12 to prevent effusion of a fluid on the temperature controlling are choked at the mouth part 51 at a tip below the temperature controlling region, respectively.

The fixed cap 123 has a heat-shrinking tube 122, and a resin cap 124 provided so as to choke a tip of the heat-shrinking tube 122 which is shrunk by heating, and a pin 126 which can be inserted and fitted into the mouth part 51 is provided in the resin cap 124. The fixed cap 123 is shrunk so as to narrow an external diameter of the small-diameter tube 52 of the disposable tip 12 by heating an upper end part of the heat-shrinking tube 122. Thereby, the cap is assuredly attached to a tip of the small-diameter tube 52, thereby, high sealing property can be obtained.

The movable cap 125, unlike the fixed cap 123, is entirely formed of a heat-shrinking material and, by heating the cap so as to be shrunk to an internal diameter approximately equal to an external diameter of the small-diameter tube 52 of the disposable tip 12, the cap is narrowed so that the small-diameter tube 52 is fitted. Thereby, the cap is assuredly attached to a tip of the small-diameter tube 52, and high sealing property can be obtained. It is preferable that the fixed cap 123, and the movable cap 125 are provided on a bottom below the insertion pore 36 in the dark box 34 in which temperature controlling is performed.

Figure 11:
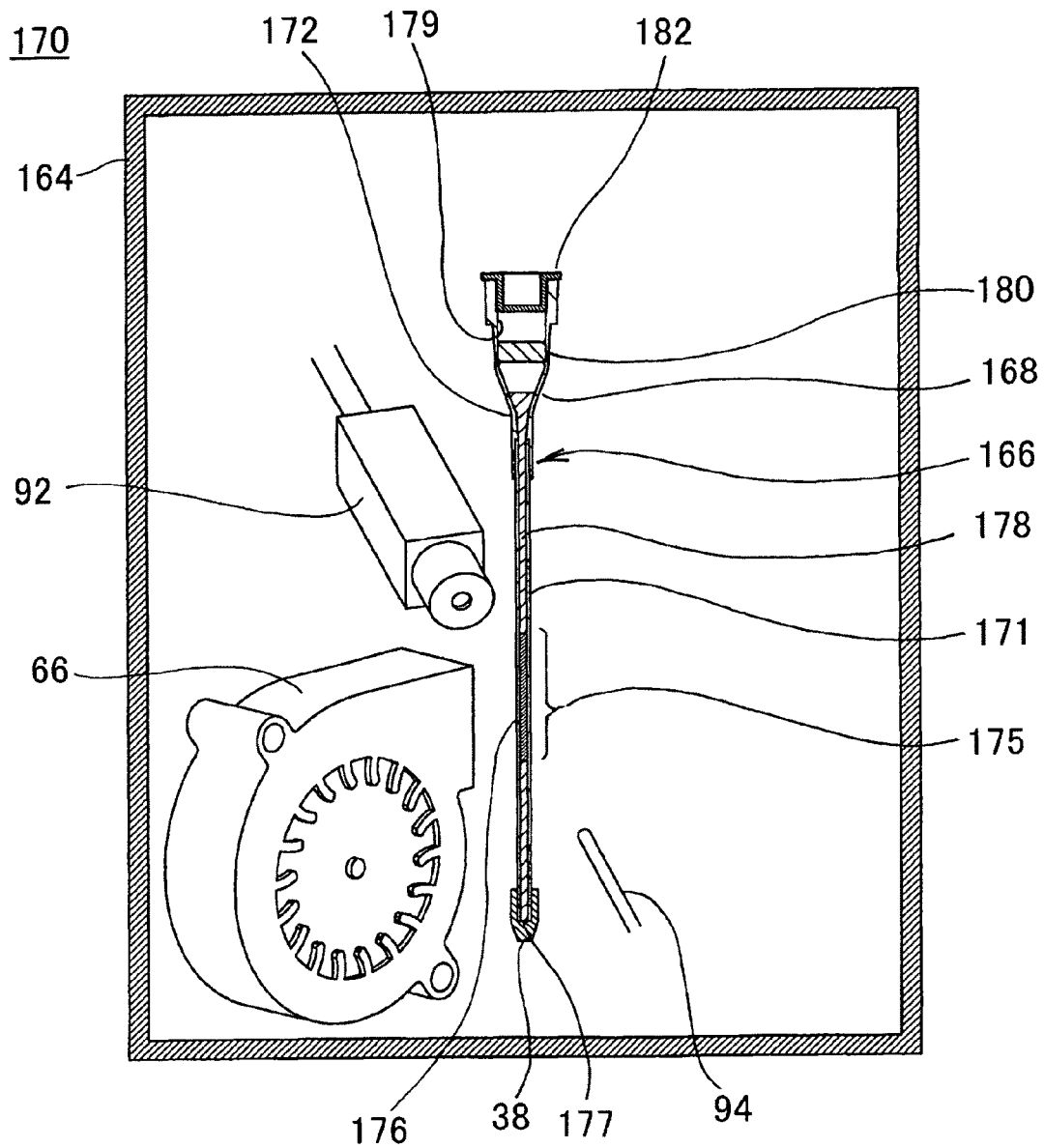
FIG. 11 is a cross-sectional view showing an example at temperature controlling and light measurement of the temperature controlling apparatus of the second embodiment.

FIG. 11 shows a temperature controlling apparatus 170 using a disposable tip 166 of a second embodiment.

The temperature controlling apparatus 170 has a dark box 164 in which temperature controlling of the disposable tip 166, and light measurement are performed. In the dark box 164, a light source 62 for excited light as the irradiation part, a light receiving optical fiber 94 as a light receiving end, and a fan 66 as a fluid source of a temperature regulator are provided so that the hot air can be ejected toward a temperature controlling region 175 described later of the disposable tip 166, and a focal point is consistent with the temperature controlling region 175 and, at the same time, the disposable tip 166 can be accommodated.

The disposable tip 166 has a large-diameter tube 168 having a mounting opening 179 to be mounted in a mounting nozzle not shown, a small-diameter tube 171 which is formed to be thinner than the large-diameter tube 168, and has a mouth part at a tip at which the temperature controlling region 175 is defined, and a funnel-like transition part 172 provided between the large-diameter tube 168 and the small-diameter tube 171.

In the large-diameter tube 168, a filter 180 for preventing contamination of the mounting nozzle divides the large-diameter tube in an axial direction, and partitions it.

In order to perform temperature controlling and light measurement, the disposable tip 166 is mounted in the mounting nozzle, a sealing liquid 178, a liquid 176 to be temperature-controlled, and a sealing liquid 178 are sucked into the small-diameter tube 171 in this order using a suction and discharge mechanism, and a position is controlled with the suction and discharge mechanism so that the liquid 176 is positioned at the temperature control region 175. Thereafter, the movable cap 38 is fitted and mounted into a mouth part 177 at a tip of the small-diameter tube 171 and, at the same time, the disposable tip 166 is detached from the mounting nozzle, and an upper side cap 182 is fitted and mounted in the mounting opening 179. In that state, they are accommodated in the dark box 164, and the temperature controlling and the light measurement are performed.

Figure 12:
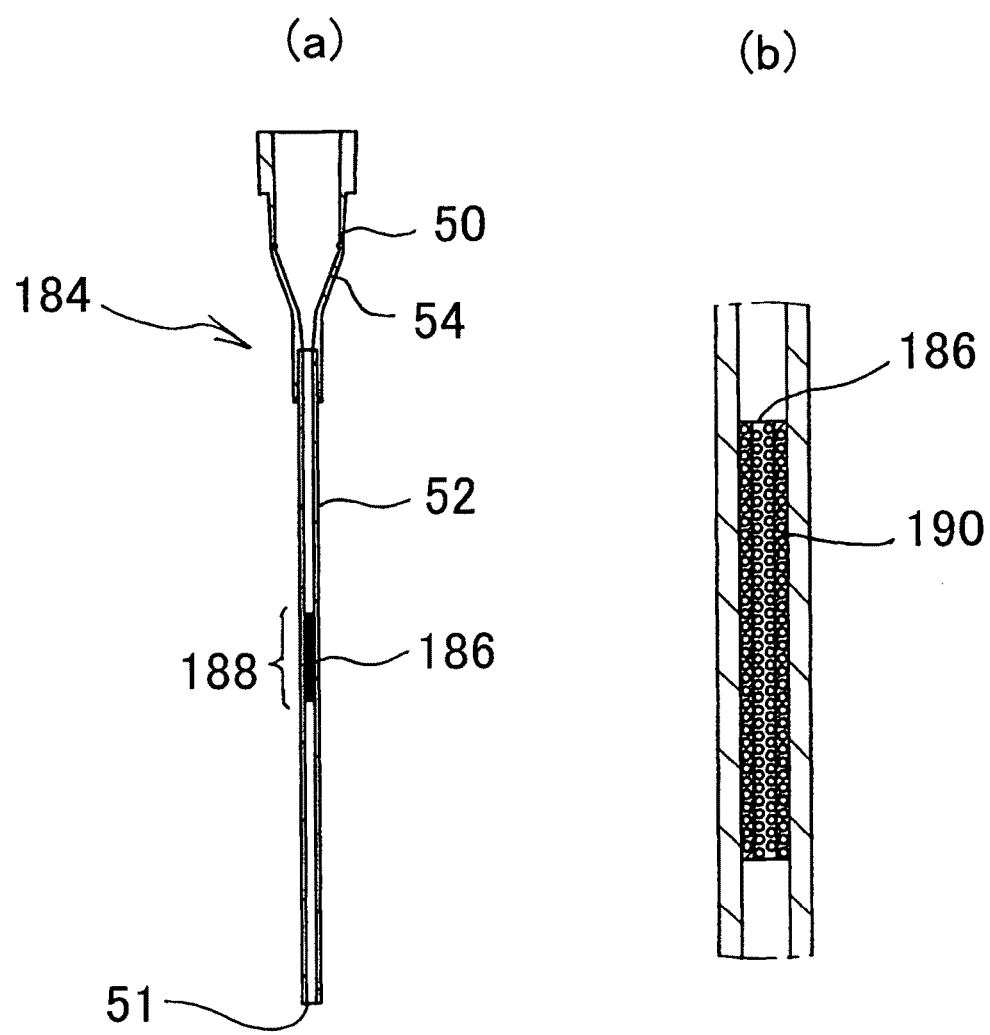
FIG. 12 is a cross-sectional view showing an example of the temperature controlling region of the temperature controlling apparatus of the third embodiment.

FIG. 12 shows a disposable tip 184 of a third embodiment.

The disposable tip 184 is such that a metal porous tube 186 having an external diameter approximately the same as an internal diameter of the small-diameter tube 52, having a length approximately equal to a length of the temperature controlling region 188, and having a surface on which many pores are perforated is inserted into and retained in a part corresponding to the temperature controlling region 188 of the small-diameter tube 52 thereof. As the metal, for example, a metal such as copper having high heat conductivity is used. According to the present embodiment, by perforating many pores, a surface area of the metal porous tube 186 is increased to extend a contact surface area between the liquid 56 to be temperature-controlled, thereby, the effect of temperature controlling is enhanced.

FIG. 13 shows the case where two kinds of thick walls (t=1 mm and 0.2 mm, an internal diameter of the small-diameter tube 52 is 1.1 mm and a length is 75 mm; the state where the water is sucked, a material is a glass) are used as the small-diameter tube 52 of the disposable tip 12, a temperature raising and lowering body 91 is contacted with an external side of the small-diameter tube 52 (temperature controlling region), this is maintained at a set predetermined temperature of Tb=94° C., 50° C. and 72° C. in this order for 5 seconds, 5 seconds, 10 seconds, respectively, thereby, temperature controlling of repeating a temperature cycle of one cycle of 30 seconds is performed, and a temperature Tw in the small-diameter tube 52 is measured.

As shown in a graph of FIG. 13, in the case of a thick wall t=1 mm, not only change of a temperature Tw at the temperature controlling region relative to change in a temperature Tb of the temperature regulator is slow, but also a difference between a temperature Tb and a temperature Tw is great, and a wall thickness is smaller, following capability of temperature controlling is high. When a delay time between peaks of a temperature Tb and a temperature Tw becomes great, a temperature Tw does not reach an objective temperature until controlling is switched to a next predetermined temperature after the temperature regulator reaches an objective determined temperature. Therefore, the wall thickness is suitably 0.2 mm or less when a temperature cycle is repeated rapidly. Temperature following capability naturally depends also on heat conductivity of a material used in the temperature controlling region. When a resin such as polypropylene is used, it is preferable that a wall thickness is around 0.1 mm.

Figure 14:
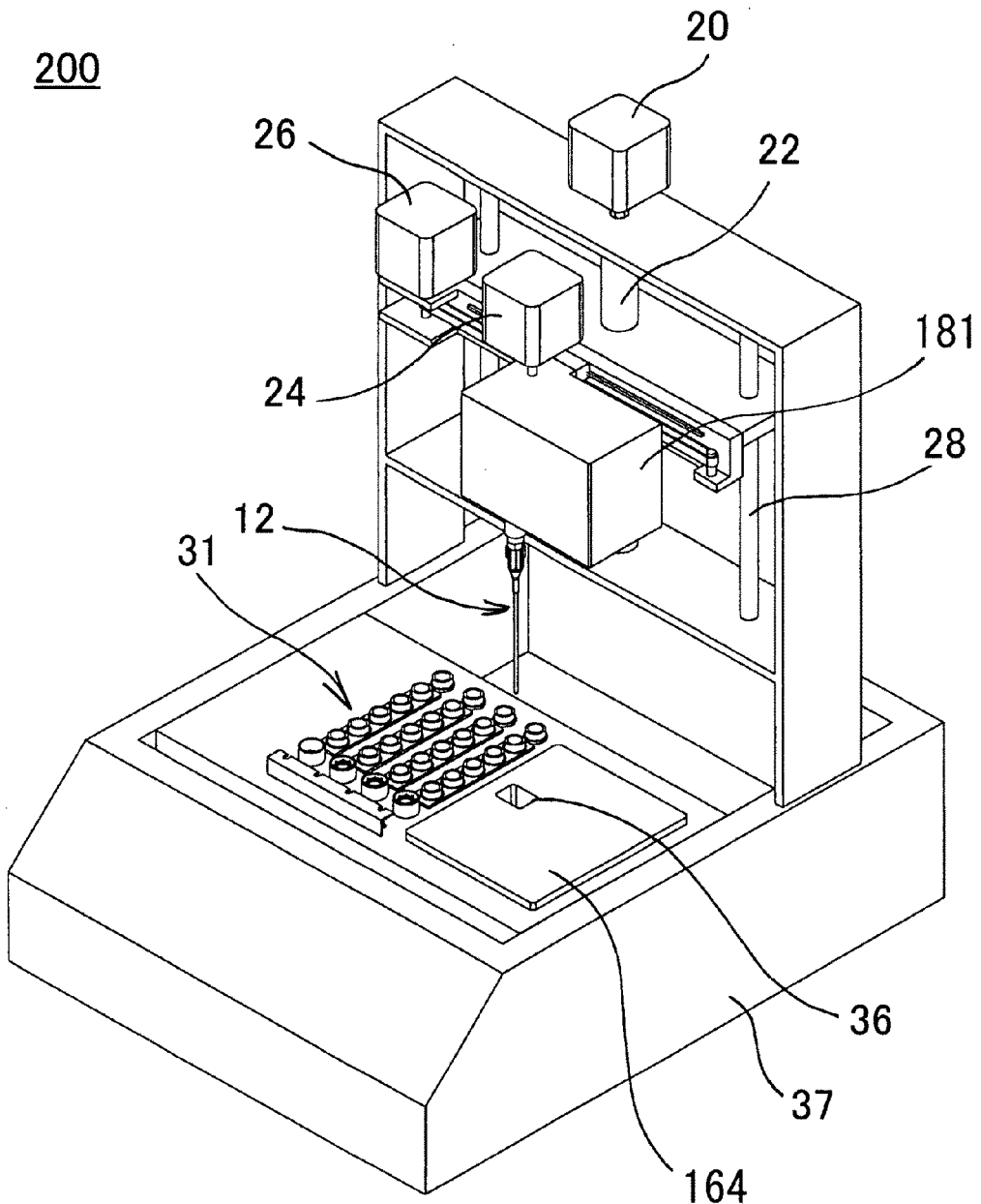
FIG. 14 is a perspective showing the temperature controlling apparatus of the fourth embodiment.

FIG. 14 shows a temperature controlling apparatus 200 of a fourth embodiment. Since the same symbols as those of the temperature controlling apparatus 10 of the first embodiment, or omitted symbols show the same things, explanation is omitted.

In the temperature controlling apparatus 10 of the first embodiment or the temperature controlling apparatus 170 of the second embodiment, the temperature regulator, and the light measurement equipment or an irradiation end or a light receiving end of the light measurement equipment are built-in in the dark boxes 36, 164, but in the temperature controlling apparatus 200 according to the present embodiment, in the dark box 164, only the temperature regulator is built-in, and a nozzle head 181 in which the light measurement equipment or the irradiation end and the light receiving end of the light measurement equipment are incorporated into the nozzle head 18 is provided. Even in this case, when light is measured, it is preferable that light is measured after the disposable tip is inserted into the dark box 164 through the insertion pore 36.

Figure 15:
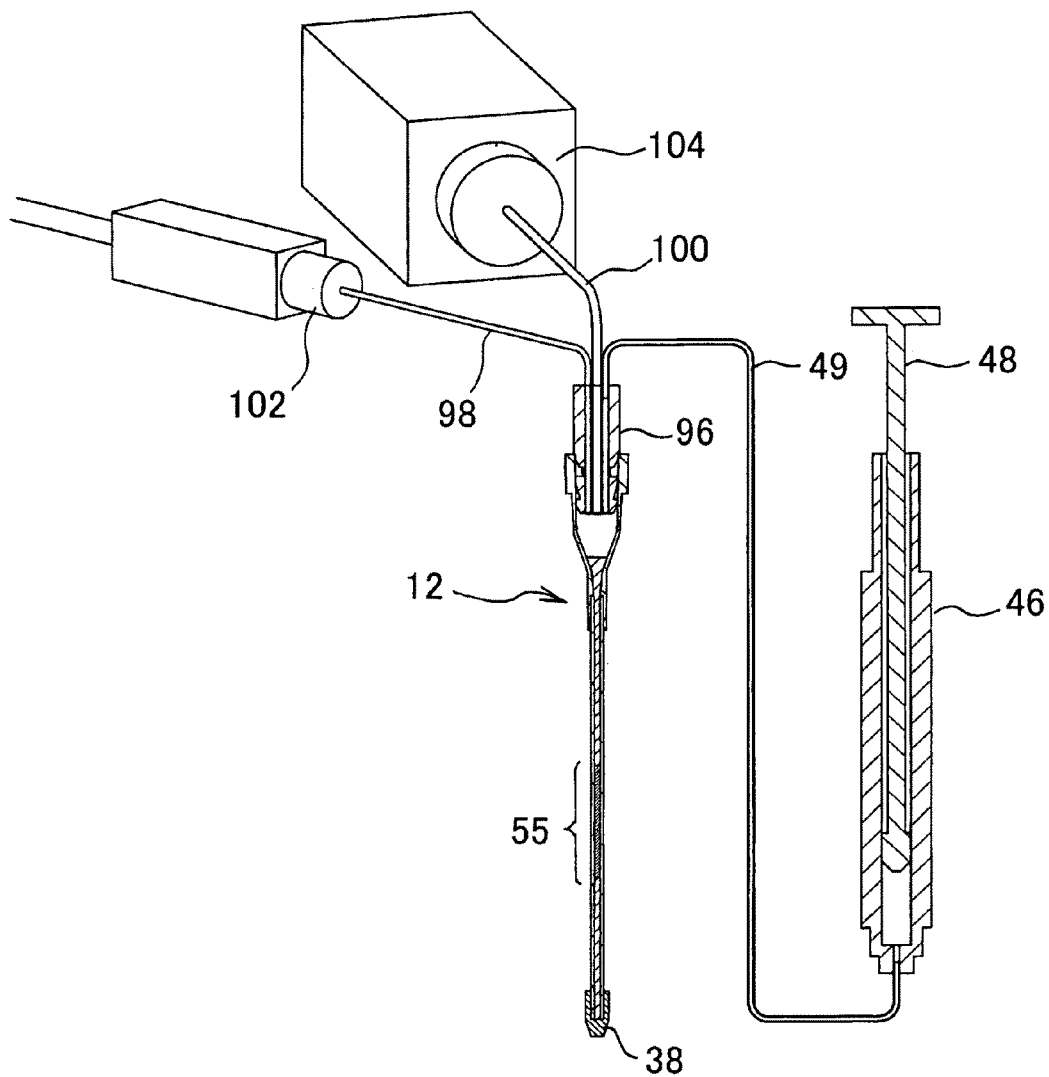
FIG. 15 is a cross-sectional view showing an example at light measurement of the temperature controlling apparatus of the fourth embodiment.

FIG. 15 shows the case where a light measuring equipment is provided, in which the temperature controlling region 55 of the disposable tip 12 is irradiated with excited light from an upper direction, and it is measured at an upper position.

The nozzle 96 of the disposable tip 12 has, in addition to a pore communicating with the flow-tube 49 of the suction and discharge mechanism, a trigger light source 102 as an irradiation part, a pore for guiding an irradiation optical fiber 98, as an irradiation end, which is optically connected to the trigger light source 102, is supported by the nozzle 96, and is provided so that the irradiation edge face reaches a tip surface of the nozzle 96, and faces an internal space contoured with the disposable tip 12, and as a light receiving part, a photoelectron multiplier tube (PMT) 104 as a photoelectric element, and a light receiving optical fiber 100, as a light receiving end, which is optically connected to the photoelectron multiplier tube 104, is supported by the nozzle 96, and is provided so that the light receiving edge surface reaches a tip surface of the nozzle 96, and faces an internal space contoured with the disposable tip 12. Herein, it is preferable that the trigger light source 102 and the photoelectron multiplier tube 104 are provided in the nozzle head 181.

Figure 16:
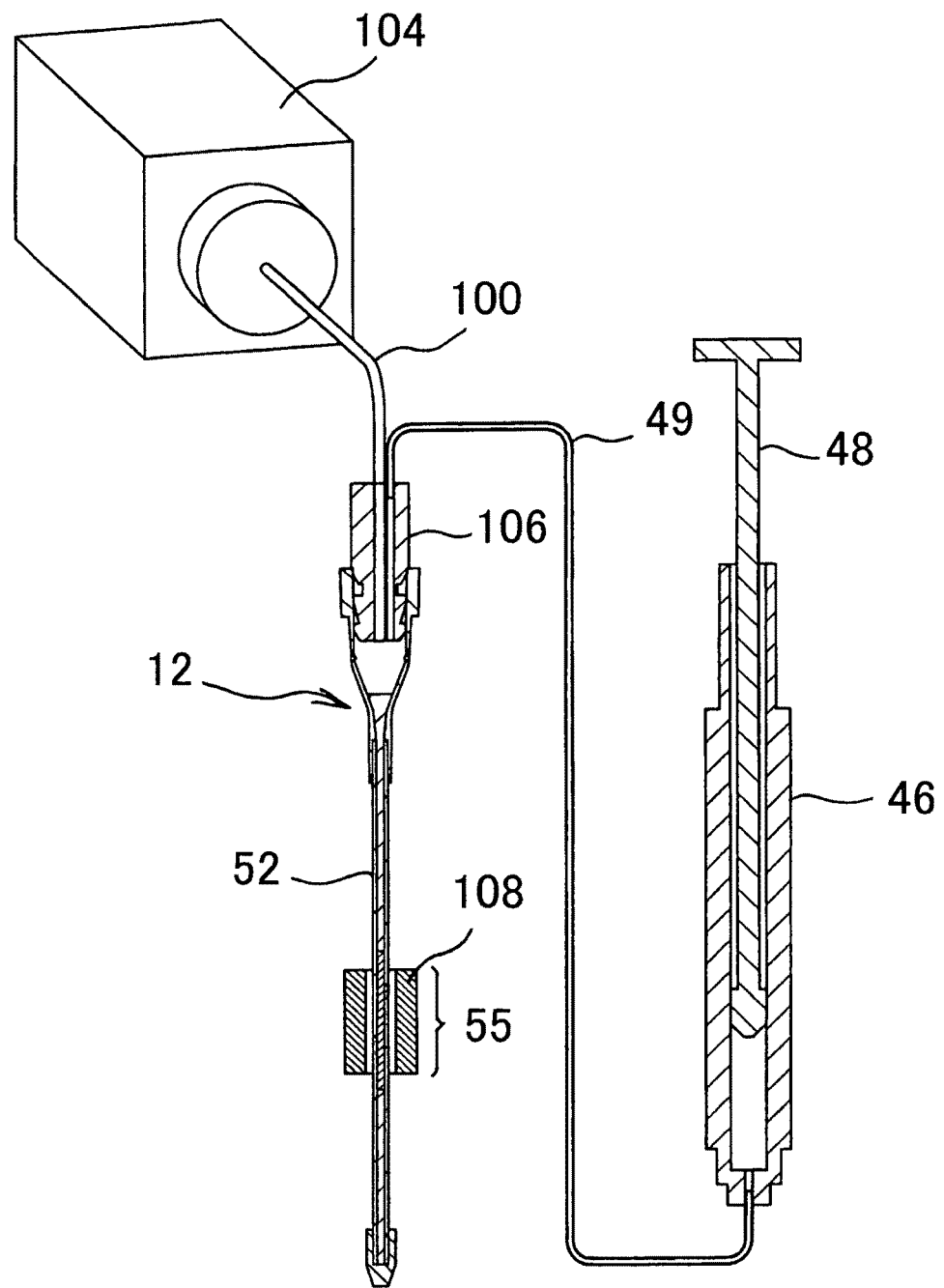
FIG. 16 is a cross-sectional view showing other example at light measurement of the temperature controlling apparatus of the fourth embodiment.

FIG. 16 shows the case where a light measurement equipment is provided, in which the temperature controlling region 55 of the disposable tip 12 is irradiated from a side direction, and measurement is performed at an upper position.

In the mounting nozzle 106 in which the disposable tip 12 is mounted, in addition to a pore communicating with the flow-tube 49 of the suction and discharge mechanism, an irradiation edge face at a tip of the light receiving optical fiber 100 as the light receiving end is attached so that it reaches a tip surface of the nozzle, and is faced with a space of the large-diameter tube contoured with the nozzle. The light receiving optical fiber 100 is connected to the photoelectron multiplier tube 104.

On the other hand, as an irradiation part, a cylindrical light source 108 having a light emitting body such as LED is movably provided along an axial direction of the small-diameter tube 52 so as to surround the small-diameter tube 52 of the disposable tip 12. An internal diameter of the cylindrical light source 108 is formed to be slightly larger than an external diameter of the small-diameter tube 52, and a height thereof is preferably a length containing a main part of the temperature controlling region 55. It is preferable that the cylindrical light source 108 is provided below the insertion pore 66 in the dark box 164, from a view point of measurement of the light. In addition, it is preferable that the light receiving part is provided in the nozzle head 181.

Figure 17:
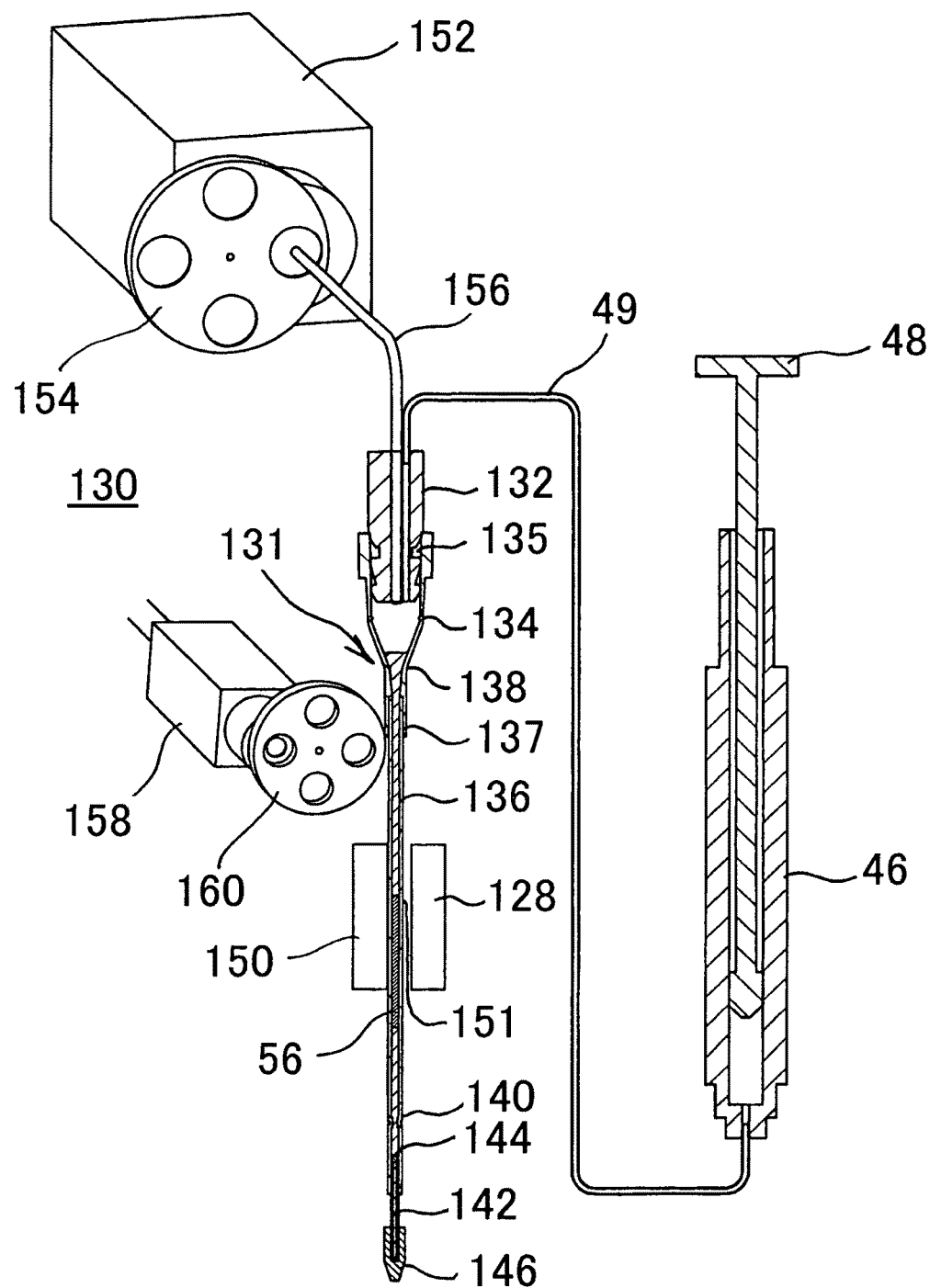
FIG. 17 is a cross-sectional view showing an example at temperature controlling and at light measurement of the temperature controlling apparatus of the fifth embodiment.

FIG. 17 is a cross-sectional view of a main part of the temperature controlling apparatus 130 using a disposable tip 131 of the fifth embodiment.

The temperature controlling apparatus 130 has the disposable tip 131 mounted in the mounting nozzle 132, and a suction and discharge mechanism. Since the same symbols as symbols used in the temperature controlling apparatus 200 of the fourth embodiment represents the same things, explanation is omitted.

The disposable tip 131 is such that a lower end of the mounting nozzle 132 is fitted into and mounted in the mounting opening 135. The mounting nozzle 132 is communicated with the cylinder 46 via the following flow-tube 49. In addition, in the mounting nozzle 132, in addition to the pore, a tip of a light receiving optical fiber 156 as a light receiving part is attached so that it reaches a tip surface of the mounting nozzle 132, and faces with a space contoured with the mounting nozzle 132 and the large-diameter tube 134. The light receiving optical fiber 156 is connected with a photoelectron multiplier tube 152 via four kinds of selectable filters 154.

On the other hand, as an irradiation part, a light source 158 is provided for irradiating excited light to a temperature controlling region 151 of the small-diameter tube 136 described later of the disposable tip 131 via four kinds of selectable filters 160.

The disposable tip 131 has a large-diameter tube 134, on an upper side of which the mounting opening 135 is provided, a small-diameter tube 135 which is formed to be smaller than the large-diameter tube 134, and in which a liquid can flow in and flow out from a tip thereof, and a funnel-like transition part 138 formed between the large-diameter tube 134 and the small-diameter tube 136. An upper end of the small-diameter tube 136 is fitted to a lower side of the transition part 138, and the part has a fitting end 137 attached with ultrasound welding, thermal welding or an adhesive. An internal diameter of the small-diameter tube 136 and an internal diameter of the transition part 138 are smoothly connected.

The small-diameter tube 136 is constructed that its axis is straight, and an internal diameter is of a constant size over a full length along an axial direction, and two protrusions 140 corresponding to the sealing part which are recessed from an external side of the small-diameter tube 136 so as to be directed innerwardly, and are protruded in a radial direction are formed near a tip thereof, so as to confront with the small-diameter tube 136. An extremely small tube 142 having a thinner internal diameter than an internal diameter of the small-diameter tube is fitted and connected to a tip of the small-diameter tube 136. The extremely small tube 142 is formed of, for example, metals such as stainless steel, inorganics such as glasses, ceramics, or organic substances of resins such as propylene, polystyrene. In a space surrounded by an upper end of the extremely small tube 142, and an internal wall of the protrusion 140 and the small-diameter tube 136, a spherical magnetic valve 144 of a magnetic body which is larger than an internal diameter of the extremely small tube 142 and gaps between the two protrusions 140, and smaller than an internal diameter of the small-diameter tube 136 is sealed, and an on-off valve as the choking member is formed. The cap 146 is further detachably fitted and mounted to a tip of the extremely small tube 142.

Further, in the small-diameter tube 136, the temperature controlling region 151 is provided, a constant temperature source 150 as a temperature regulator set at a predetermined temperature is provided contacting with the temperature controlling region 151, and a constant temperature source 128 as a temperature regulator set at different temperatures is provided, departed from a side surface of the temperature controlling region 151. Herein, the light source 158, and constant temperature sources 128, 150 are provided in the dark box 164, and the photoelectron multiplier tube 152 is provided in the nozzle head 181.

Figure 18:
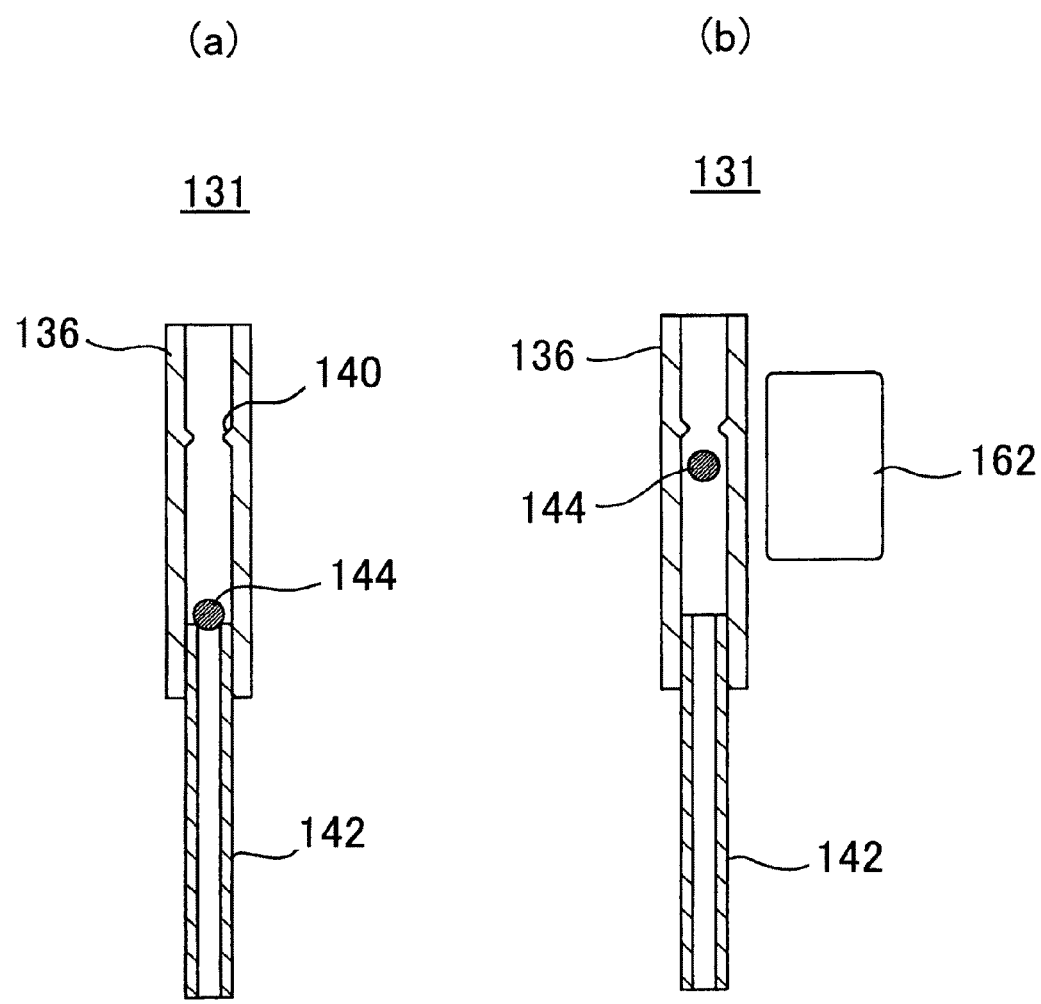
FIG. 18 is a partially enlarged cross-sectional view of FIG. 17.

FIG. 18 shows enlargement of vicinity of a tip of the disposable tip 131 of the fifth embodiment. FIG. 18(A) shows the state where the magnetic valve 144 is fallen by its own weight to choke an opening of an upper end of the extremely small tube 142. FIG. 18(B) shows a magnetic force body 162 corresponding to the on-off mechanism, and a magnetic force device (not shown) moving the magnetic force body 162 in up and down directions. The state where by moving and retaining the magnetic valve 144 of the on-off valve to up direction using the magnetic force body 162, an opening of an upper end of the extremely small tube 142 is shown.

Figure 19:
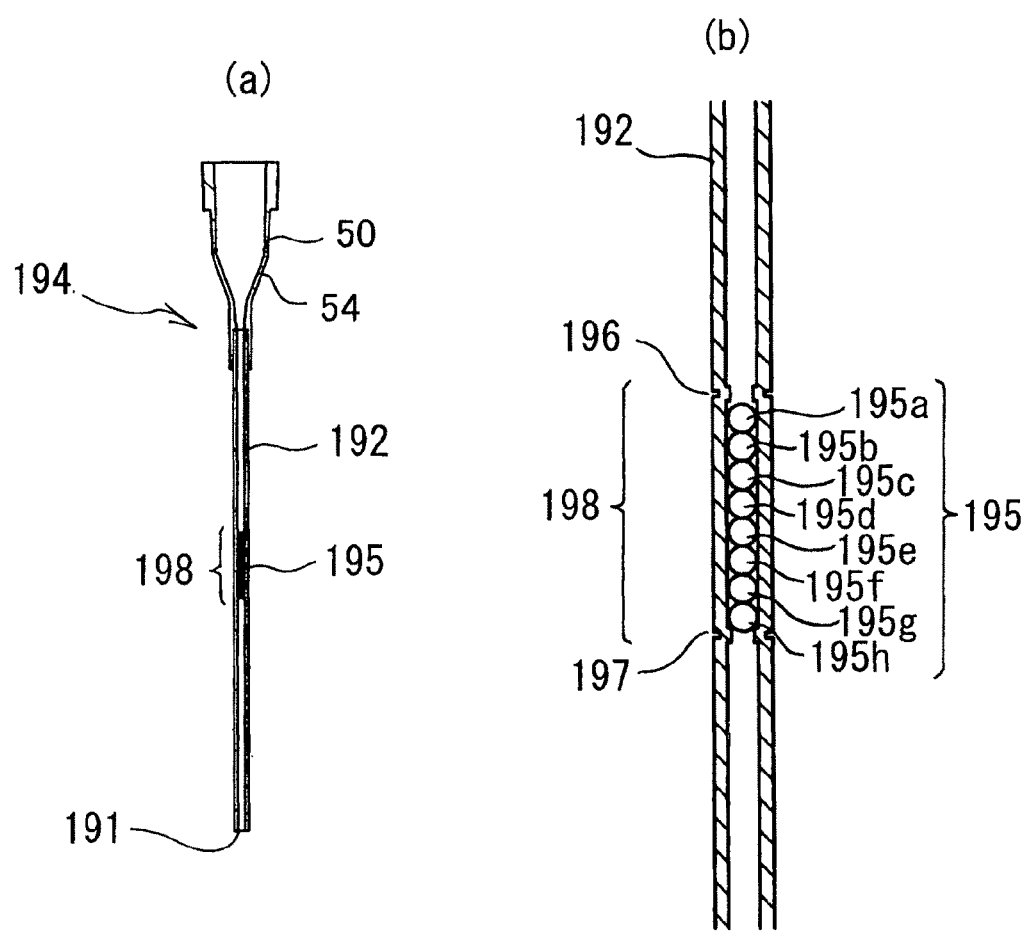
FIG. 19 is a cross-sectional view showing the Particle-like carrier-encapsulated tip of the sixth embodiment.

Based on FIG. 19, the temperature controlling apparatus using a particle-like carrier-encapsulated tip 194 of the sixth embodiment is explained.

The particle-like carrier-encapsulated tip 194 is such that a particle-like carrier 195 is encapsulated in the disposable tip 12. In a temperature controlling region 198 of a small-diameter tube 192 of the particle-like carrier-encapsulated tip 194, a plurality of (8 in this example) particle-like carriers 195 are encapsulated. The particle-like carrier 195 is encapsulated by swaging the small-diameter tube 192 so that a liquid can pass, but the particle like carrier 195 cannot pass, at an upper end and a lower end of the temperature controlling region 198 of the small-diameter tube 192. Herein, a diameter of the particle-like carrier 195 is about 1 mm, and an internal diameter of the small-diameter tube 192 is about 1 mm or more. The particle-like carrier 195 can be passed by a liquid, but a liquid can be also encapsulated using a member such as a filter through which the particle-like carrier cannot pass, or the small-diameter tube having such the shape.

Then, the case of application of temperature controlling treatment using the particle-like carrier-encapsulated tip 194 of the sixth embodiment shown in FIG. 19 in place of the disposable tip 12 of the temperature controlling apparatus 10 shown in FIG. 1 to nucleotide sequence detection treatment of detecting whether a predetermined nucleotide sequence is present in a DNA to be detected or not, will be explained.

The treatment has a sealing step S1 of extracting a DNA to be detected from a subject or an unknown bacterium, accommodating a solution in a container, preparing a plurality of (in this case, 8) particle-like carriers 195a, 195b, 195c, 195d, 195e, 195f, 195g, and 195h to which a plurality of kinds of prepared primers 193a, 193b, 193c, 193d, 193e, 193f, 193g, and 193h having a plurality of kinds of nucleotide sequences presumed to be present in the obtained DNA are bound chemically (chemical bond includes covalent bond, ion bond, metal bond etc.), as the particle-like carrier 195 of the particle-like carrier-encapsulated tip 194, and sealing them into the small-diameter tube 192, a bonding step S2 of annealing or hybridizing the primer 193a to primer 193h of the particle-like carrier 195, and the primer 193 having the nucleotide sequence complementary with a nucleotide sequence contained in a DNA 201 which is the extracted gene or a template gene, a washing step S3 of removing the DNA 201 which has not been bound with the particle-like carrier 195a to particle-like carrier 195h, and debris by washing, an amplification step S4 of placing reverse primer 204a to reverse primer 204h of a corresponding DNA labeled with a fluorescent substance or the like, and performing amplification by the PCR method, and a detection 4 of performing detection of light emission after washing. The particle-like carrier 195 to be prepared is a size of, for example, a diameter of around 1 mm and, for example, various resins such as nylon (manufactured by Polysciences) are used. Besides, for example, ceramics (alumina 1.88 mm diameter, manufactured by Chiba Ceramics) can be used. When a light sealing particle is also contained in the particle-like carrier 195, for example, color glasses of a diameter of 2.0 mm are used. As the small-diameter tube 192, for example, a tube made of polypropylene is used, and a size thereof is slightly larger than a diameter of a particle-like carrier.

Using FIG. 20 and FIG. 21, the nucleotide sequence detection treatment is explained in detail below.

Figure 20:
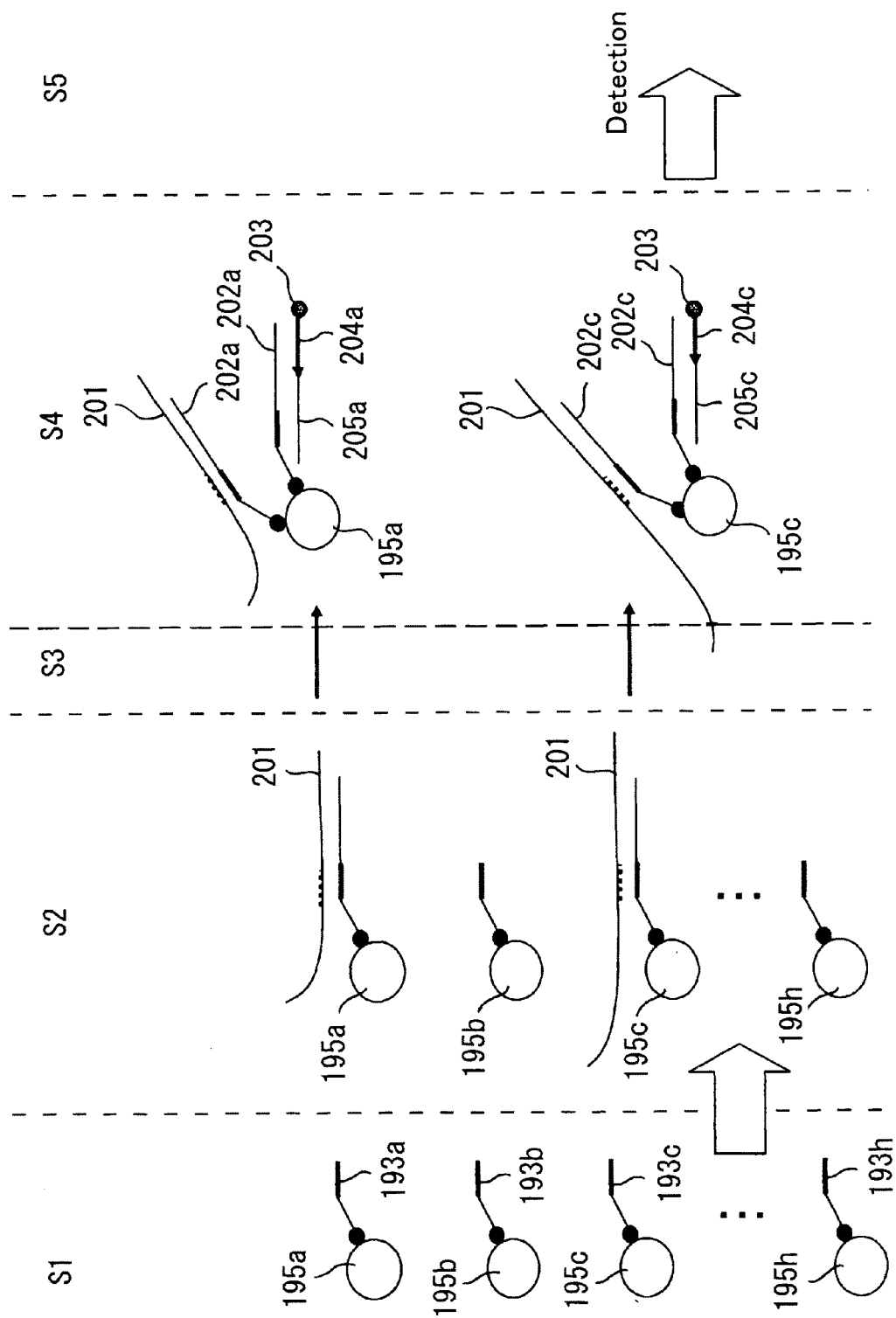
FIG. 20 is a flow chart of a treatment example using the particle-like carrier-encapsulated tip of the sixth embodiment.
Figure 21:
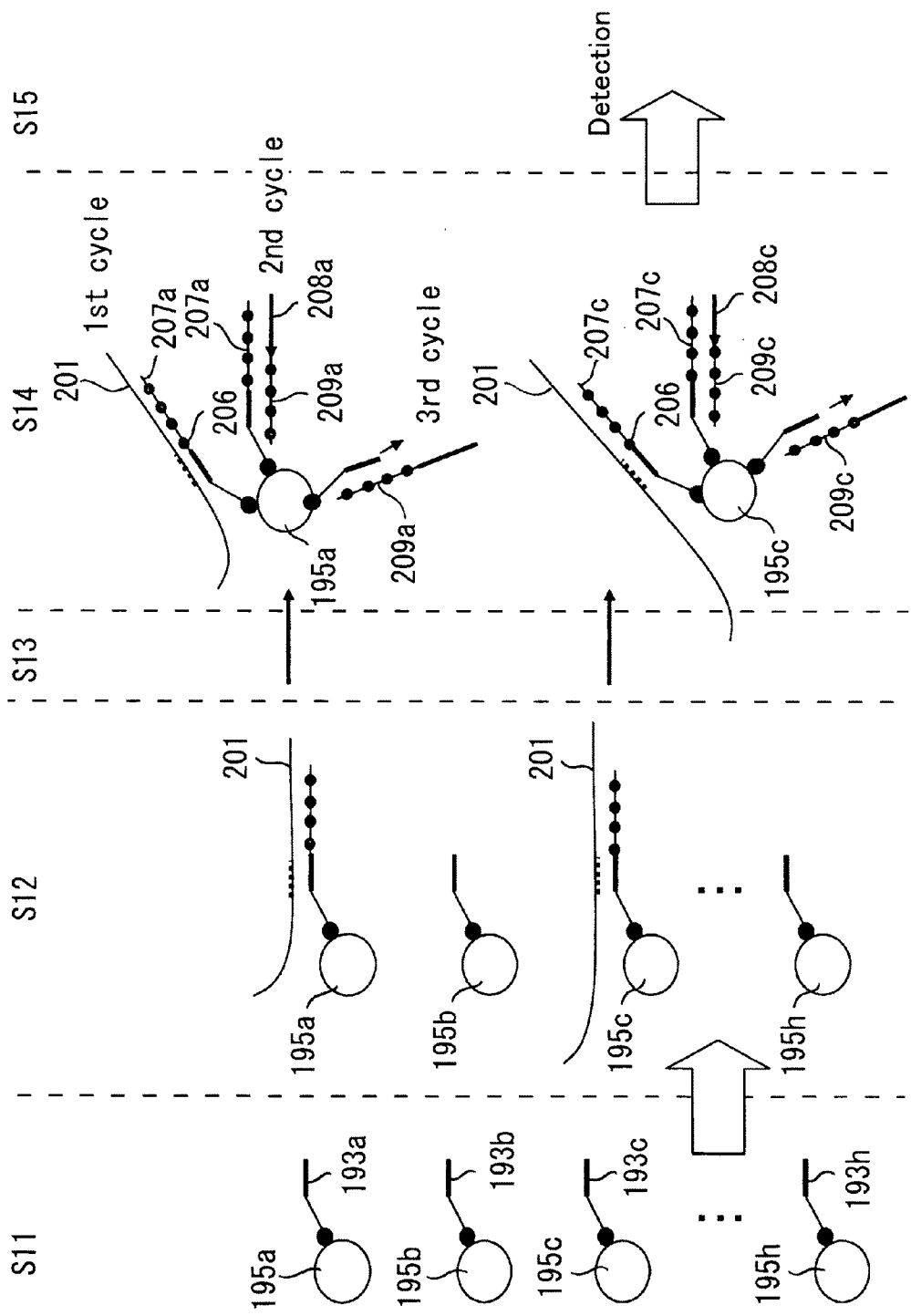
FIG. 21 is a flow chart of other treatment example using the particle-like carrier-encapsulating tip of the sixth embodiment.

As shown in FIG. 20, the encapsulating step of step S1 has, for example, a collection step of collecting from a subject a specimen such as an oral cavity mucous membrane, blood, a nail, respectively, accommodating a solution of a DNA extracted therefrom or a template DNA into a predetermined container of the container group 31, a step of chemically modifying a surface of 8 particle-like carriers 195, and binding eight kinds of primer 193a to primer 193h having a nucleotide sequence presumed to be possessed by the DNA of a subject of the specimen to the particle-like carrier 195a to particle-like carrier 195h, respectively, and a step of introducing the particle-like carrier 195a to particle-like carrier 195h in this order so that they are arranged in the small-diameter tube 192 downwardly, swaging the small-diameter tube 192 at its upper end 196 and its lower end 197, and encapsulating the particle-like carrier 195 in the temperature controlling region 198 to prepare a particle-like carrier-encapsulated tip 194.

In the binding step of step S2, the particle-like carrier-encapsulated tip 194 is mounted in the mounting nozzle 14 of the temperature controlling apparatus 10, the particle-like carrier-encapsulated tip 194 is moved using the movement mechanism, a tip of the particle-like carrier-capsulated tip 194 is inserted into the container in which a solution containing a collected DNA 201 or a template DNA 201 prepared from the DNA is contained, and the solution is sucked using the suction and discharge mechanism.

Then, using the movement mechanism, the particle-like carrier-encapsulated tip 194 is moved while the solution is sucked, a tip of the particle-like carrier-encapsulated tip 194 is inserted into the movable cap 38 penetrating the notch part 42 of the cap detachment horizontal plate 40, thereby, the movable cap 38 is mounted in the mouth part 191 of the particle-like carrier-encapsulated tip 194 to choke the mouth part 191, this is moved in a horizontal direction, the particle-like carrier-encapsulated tip 194 is inserted into the dark box 34 through the insertion pore 36, the temperature controlling region 198 is heated using the temperature regulator such as a fan to degenerate the DNA 201 to dissociate into single-stranded chains and, when primer 193a to primer 193h having a nucleotide sequence complementary with a nucleotide sequence presumed to be contained in the DNA 201 is present, the chains are made to be annealed or hybridized. After completion of annealing or hybridization, a temperature of the temperature controlling region 198 is lowered using the temperature regulator, for example, the fan 66.

In the washing step of step S3, the particle-like carrier-encapsulated tip 194 is extracted from the insertion pore 36 using the movement mechanism, the movable cap 38 is detached using the cap detaching horizontal plate 40, this is moved to a position of a container accommodating a washing solution of the container group 31, the mouth part 191 at a tip of the particle-like carrier-encapsulated tip 194 is inserted into the container, and suction and discharge of the accommodated washing solution are repeated to perform washing, thereby, the DNA 201 which has not been bound to the particle-like carrier 195 is washed off.

In the amplification step of step S4, the particle-like carrier-encapsulated tip 194 is moved using the movement mechanism, to a container in the container group 31 accommodating a buffer containing a polymerase, reverse primer 204a to reverse primer 204h labeled with fluorescence 203 (or Dig) regarding a predetermined DNA which is desired to be amplified, bases and the like, and the buffer is sucked with the suction and discharge mechanism. The particle-like carrier-encapsulated tip 194 is moved while the buffer is sucked, the movable cap 38 is mounted again at a tip of the particle-like carrier-encapsulated tip 194, this is passed through the insertion pore 36, the particle-like carrier-encapsulated tip 194 is inserted again in the dark box 34, and temperature controlling is performed according to the PCR method using the temperature regulator. Thus, at a first cycle, elongation of DNA 202a and DNA 202c is initiated using a DNA 201 as a template, at a second cycle, elongation of DNA 205a, and DNA 205c from a reverse primer 204a, and a reverse primer 204c is initiated using the elongated DNA 202a and DNA 202c as a template and, at a third cycle, elongation of a DNA from primers fixed on the particle-like carrier 195 is initiated using DNA 205a, and DNA 205c elongated from the reverse primer as a template.

Then, after completion of a predetermined cycle, DNA 202a and DNA 202c bound to the particle-like carrier 195 are amplified, therefore, the DNA light emission intensity is also amplified, and light emission is measured with a light measuring machine in the dark box 34 regarding the relevant DNA 202a and DNA 202c, in the detection step of S5. From this result, a nucleotide sequence present in the DNA 201 and a nucleotide sequence not present therein are specified.

In the case of a fluorescent label, for example, the step is performed, for example, with the trigger light source 92, and the light receiving optical fiber 94 as a light receiving end for receiving light emission of a fluorescent substance. On the other hand, when labeled with Dig, since after reacted with a HRP labeled anti-Dig antibody, light is emitted using a substrate solution, movement of the particle-like carrier-encapsulated tip 194 becomes necessary.

Subsequently, based on FIG. 21, other nucleotide solution sequence detection treatment will be explained.

The treatment has an encapsulation step of step S11, a binding step of step S12, a washing step of step S13, and a detection step of step S15 as same as the treatment and, in the amplification step of step S14, unlike the amplification step of step S4 of the treatment, amplification is performed using Dig-dNTP206 (or fluorescently labeled dNTP) in a part of nucleotides and, instead, the reverse primer 208a to reverse 208h are not labeled. In this case, an efficiency of amplification is slightly reduced as compared with the aforementioned treatment, but since a light emission intensity is high, detection can be easily and assuredly performed. In addition, Dig-dNTP206 (or fluorescently labeled dNTP) in place of bases is incorporated into DNA 209a and DNA 209c elongated from reverse primer 208a, and reverse primer 208c using elongated and amplified DNA 207a, and DNA 207c, and elongated DNA 207a and DNA 207c as a template.

In addition, in the encapsulation step S1 or the encapsulation step S11, regarding the particle-like carrier 195, the primer 193a to primer 193h are bound, respectively, and at the same time, an antibody may be fixed on the particle-like carrier 195 for capturing a DNA on the particle-like carrier 195, and an antigen may be bound to the DNA 201. Thereby, the DNA 201 to be amplified by the PCR method may be pulled towards the particle-like carrier 195. Then, by temperature controlling in the amplification step, the antibody is inactivated, and the DNA 201 is collected near the particle-like carrier 195, thereby, amplification is effectively performed.

In addition, upon implementation of the PCR method, as a labeling substance to be incorporated, Biotiin-dNTP can be utilized in addition to Dig, and a fluorescent label. In this case, light emission detection using Avidin-HRP, or detection using a fluorescently labeled Avidin is possible.

In addition to the above example, Dig-dNTP, and an AP-labeled anti-Dig antibody and a POD-labeled anti-Dig antibody specifically bounded to Dig-dNTP can be also used. In place of discrimination by a position of a sequence of the particle-like carrier, in the case of implementation of mutually distinguishable different labeling, an order of a sequence of particle-like carriers can be randomized.

The forgoing embodiments were specifically explained for better understanding of the present invention, but do not limit another embodiment. Therefore, variation is possible in such the range that the gist of the invention is not changed. For example, as explained, both of temperature regulation and light measurement were performed in a dark box, but temperature controlling may be performed outside the dark box. Alternatively, the temperature regulator can be also provided on the nozzle head. In addition, in the foregoing embodiments, only the PCR method was explained, treatment using various enzymes, and treatment of proteins or the like can be also used in temperature controlling of a liquid, being not limited to the PCR method.

In addition, the temperature regulator, the light measuring equipment, the disposable tip, the particle-like carrier-encapsulated tip, the labeling element, the nozzle, the suction and discharge mechanism, the choking member, the reagent, the container and the like, which were explained in each embodiment of the present invention, may be properly selected, and may be mutually combined by proper alternation.

INDUSTRIAL APPLICABILITY

The present invention is mainly related to every field such as treatment regarding a biological substance such as a DNA, a RNA, a mRNA, a rRNA, a tRNA, a plasmid, particularly, a genetic substance, field requiring test and analysis, for example, the industrial field, agricultural field such as foods, agricultural product, seafood processing, pharmaceutical field, medical field such as hygiene, health, disease, heritage, the science field such as biochemistry, biology. The present invention can be used, particularly, in analysis and treatment handling various DNAs such as PCR, real time PCR.

EXPLANATION OF SYMBOLS 10, 130, 170, 200 Temperature controlling apparatus
12, 131, 166 Disposable tip (nozzle)
14, 96, 106, 132 Mounting nozzle (nozzle)
38 Movable cap (choking member)
52 Small-diameter tube
55, 82, 84, 151 Temperature controlling region
64, 86, 88, 91 Temperature raising and lowering body (temperature regulator)
66 Fan (temperature regulator)
70, 72, 74, 76, 78, 81, 150 Temperature constant source (temperature regulator)
92 Trigger light source (irradiation part)
94 Light receiving optical fiber (light receiving part)

The invention claimed is:

1. A temperature controlling apparatus comprising one or a plurality of sets of nozzles which can suck and discharge a liquid through a tip, and can retain the sucked liquid, a suction and discharge mechanism which can suck and discharge a gas via the each nozzle, a temperature regulator which can maintain one or two or more set predetermined temperatures for a predetermined time regarding one or two or more predetermined temperature controlling regions provided in the each nozzle, a movement mechanism which allows relative movement between one or two or more containers which can accommodate a liquid and the nozzle, and a controlling part which instructs the movement mechanism, the suction and discharge mechanism or the temperature regulator to adjust a liquid to be sucked into the nozzle and a liquid amount thereof, a position of the sucked liquid in the nozzle, and temperature controlling of the liquid;

wherein the nozzle is provided movably relative to a container capable of accommodating a liquid to be temperature-controlled, and a container capable of accommodating a sealing liquid for sealing the liquid in the nozzle by holding it from upper and lower directions in the nozzle by the movement mechanism;

wherein a nozzle choking member which can choke the nozzle to prevent flow-out of a fluid from the nozzle is provided below a temperature controlling region of the nozzle or the outside of the nozzle, and further includes an on-off mechanism which opens and closes the nozzle below the temperature controlling region using the choking member;

wherein the nozzle includes a mounting nozzle and a disposable tip including a mounting opening detachably mounted to the mounting nozzle and a mouth part which can suck and discharge a liquid at a tip; and wherein the disposable tip includes a large-diameter tube, a small-diameter tube formed to be thinner than the large-diameter tube, and a transition part formed between the large-diameter tube and the small-diameter tube, and the temperature controlling region is set in the small-diameter tube.

2. The temperature controlling apparatus according to claim 1, wherein the controlling part instructs the movement mechanism or the suction and discharge mechanism to choke and pressurize the nozzle below the temperature controlling region of the nozzle upon temperature controlling.

3. The temperature controlling apparatus according to claim 1, the small-diameter tube is formed so that an axis is straight, and an internal diameter thereof is a constant size along an axial direction, and a size of an internal diameter thereof is 3 mm or less and 0.1 mm or more.

4. The temperature controlling apparatus according to claim 1, wherein the temperature regulator includes one or two or more temperature raising and lowering bodies which are provided so as to contact with or come close to a side wall of the temperature controlling region of the nozzle, and can raise and lower a temperature.

5. The temperature controlling apparatus according to claim 1, wherein the temperature regulator includes one or two or more temperature controlling sources which are provided so as to relatively come close to or to be departed from a side wall of the temperature controlling region of the nozzle, and are set at a predetermined temperature.

6. The temperature controlling apparatus according to claim 1, wherein the temperature regulator includes one or two or more fluid sources which flow a fluid at a predetermined temperature so as to contact with or come close to the temperature controlling region of the nozzle.

7. The temperature controlling apparatus according to claim 1, including a light measuring equipment for measuring light emission in the temperature controlling region of the nozzle.

8. The temperature controlling apparatus according to claim 7, wherein the light measuring equipment includes at least a light receiving end, and the nozzle is provided movable relative to the light receiving end by the movement mechanism.

9. The temperature controlling apparatus according to claim 1, wherein the apparatus includes a movable cap which is fittable with a tip of the nozzle, and can be conveyed, or a fixed cap which is fittable with a tip of the nozzle, and cannot be conveyed, as the choking member, the nozzle is provided movably relative to the movable car or the fixed cap, or the on-off mechanism includes the movement mechanism.

10. The temperature controlling apparatus according to claim 1, wherein in the temperature controlling region of the nozzle, a plurality of kinds of chemical substances are fixed, a plurality of fixable particle-like carriers, or an aggregate of a plurality of sets of particle-like carriers is sealed in the nozzle so as to contact with a sucked liquid and, at the same time, particle-like carriers or an aggregate of particle-like carriers to which the chemical substance is fixed or can be fixed, and the chemical substance are associated so as to be measured from the outside.

11. A temperature controlling method comprising:

a suction step of moving one or a plurality of sets of nozzles relative to one or two or more containers accommodating a liquid, and sucking a designated liquid amount of a designated liquid into one or a plurality of sets of nozzles, a liquid position adjusting step of positioning the liquid in any of one or two or more temperature controlling regions set at one or two or more predetermined temperatures, respectively, set in the each nozzle, based on the liquid amount, and a temperature controlling step of performing temperature controlling of the liquid situated at the temperature controlling region;

wherein the suction step includes a step of sucking an upper side sealing liquid, a step of sucking the liquid to be temperature-controlled, and a step of sucking a lower side sealing liquid;

wherein the method further comprises a choking step of choking the nozzle below the temperature controlling region using the choking member, before the temperature controlling step or after the liquid position adjusting step;

wherein the nozzle includes a mounting nozzle and a disposable tip including a mounting opening detachably mounted to the mounting nozzle and a mouth part which can suck and discharge a liquid at a tip;

wherein the disposable tip includes a large-diameter tube, a small-diameter tube formed to be thinner than the large-diameter tube, and a transition part formed between the large-diameter tube and the small-diameter tube, and the temperature controlling region is set in the small-diameter tube; and wherein the method further includes a mounting step of mounting the disposable tip in the mounting nozzle before the suction step.

12. The temperature controlling method according to claim 11, wherein in the temperature controlling step, the nozzle is choked, and a liquid is pressurized below the temperature controlling region of the nozzle.

13. The temperature controlling method according to claim 11, wherein the temperature controlling step includes a step of raising or lowering a temperature of one or two or more temperature raising and lowering bodies provided so as to contact with or come close to a side wall one or two or more temperature controlling regions of the nozzle.

14. The temperature controlling method according to claim 13, wherein the temperature controlling step includes a step of moving the temperature raising and lowering body, the constant temperature source or the fluid source relative to the one or two or more temperature controlling regions of the nozzle.

15. The temperature controlling method according to claim 11, wherein the temperature controlling step includes a step of relatively making one or two or more constant temperature sources set at one or two or more predetermined temperatures come close to or being departed from a side wall of one or two or more temperature controlling regions of the nozzle.

16. The temperature controlling method according to claim 15, wherein the temperature controlling step includes a step of moving the temperature raising and lowering body, the constant temperature source or the fluid source relative to the one or two or more temperature controlling regions of the nozzle.

17. The temperature controlling method according to claim 11, wherein the temperature controlling step flows a gas of one or two or more predetermined temperatures using a fluid source so as to contact with or come close to the one or two or more temperature controlling regions of the nozzle.

18. The temperature controlling method according to claim 11, wherein the temperature controlling step includes a step of moving the temperature raising and lowering body, the constant temperature source or the fluid source relative to the one or two or more temperature controlling regions of the nozzle.

19. The temperature controlling method according to claim 11, further including a light measuring step of measuring light in the temperature controlling region of the nozzle.

20. The temperature controlling method according to claim 11, wherein the suction step sucks the liquid to be temperature-controlled at a liquid amount to a degree of overflowing the temperature controlling region in the nozzle, and the position adjusting step adjusts a position so that the liquid overflows the temperature controlling region at upper and lower positions.

21. The temperature controlling method according to claim 11, further including a step of discharging a liquid accommodated in the nozzle into one or two or more containers.

22. The temperature controlling method according to claim 11, wherein in the temperature controlling region of the nozzle, a plurality of kinds of chemical substances are fixed, a plurality of fixable particle-like carriers, or an aggregate of a plurality of sets of particle-like carriers is sealed in the nozzle so as to contact with a sucked liquid and, at the same time, particle-like carriers or an aggregate of particle-like carriers to which the chemical substance is fixed or can be fixed, and the chemical substance are associated so as to be measured from the outside.

* * * * *

UNITED STATES PATENT AND TRADEMARK OFFICE
CERTIFICATE OF CORRECTION

PATENT NO. : 8,418,929 B2
APPLICATION NO. : 12/450672
DATED : April 16, 2013
INVENTOR(S) : Hideji Tajima Page 1 of 1

It is certified that error appears in the above-identified patent and that said Letters Patent is hereby corrected as shown below:

In the Specifications

Column 5, line 65, change "amounting" to -- a mounting --.

Column 5, line 67, change "amounting" to -- a mounting --.

Column 6, line 12, change "amounted" to -- a mounted --.

Column 10, line 37, change "amounted" to -- a mounted --.

Column 13, line 21, change "maybe" to -- may be --.

Signed and Sealed this
Eleventh Day of June, 2013

Teresa Stanek Rea
*Acting Director of the United States Patent and Trademark Office*